United States Patent [19]

Osborn, III et al.

[11] Patent Number: 5,772,648
[45] Date of Patent: Jun. 30, 1998

[54] ABSORBENT ARTICLE HAVING TUCKED FLAPS

[75] Inventors: Thomas W. Osborn, III, Cincinnati; Bruce William Lavash, West Chester, both of Ohio

[73] Assignee: The Procter & Gamble Company, Cincinnati, Ohio

[21] Appl. No.: 743,571

[22] Filed: Nov. 4, 1996

Related U.S. Application Data

[63] Continuation of Ser. No. 632,733, Apr. 15, 1996, abandoned, which is a continuation of Ser. No. 134,325, Oct. 7, 1993, abandoned, which is a continuation of Ser. No. 906,629, Jun. 30, 1992, Pat. No. 5,281,209.

[51] Int. Cl.$^6$ .............................. A61F 13/15; A61F 13/20
[52] U.S. Cl. ........................ 604/385.1; 604/358; 604/389
[58] Field of Search .............................. 604/358, 385.1, 604/385.2, 386, 389

[56] References Cited

U.S. PATENT DOCUMENTS

| | | |
|---|---|---|
| 3,397,697 | 8/1968 | Rickard . |
| 3,929,134 | 12/1975 | Karami . |
| 4,166,464 | 9/1979 | Korpman . |
| 4,285,343 | 8/1981 | McNair . |
| 4,327,732 | 5/1982 | Thinnes . |
| 4,496,359 | 1/1985 | Pigneul . |
| 4,589,876 | 5/1986 | Van Tilburg . |
| 4,596,570 | 6/1986 | Jackson et al. . |
| 4,597,759 | 7/1986 | Johnson . |
| 4,605,404 | 8/1986 | Sneider . |
| 4,608,047 | 8/1986 | Mattingly . |
| 4,615,696 | 10/1986 | Jackson et al. . |
| 4,654,040 | 3/1987 | Luceri . |
| 4,687,478 | 8/1987 | Van Tilburg . |
| 4,690,680 | 9/1987 | Higgins . |
| 4,692,163 | 9/1987 | Widlund et al. . |
| 4,701,171 | 10/1987 | Boland et al. . |
| 4,701,174 | 10/1987 | Johnson . |
| 4,701,178 | 10/1987 | Glaug . |
| 4,704,114 | 11/1987 | Wilson et al. . |
| 4,747,846 | 5/1988 | Boland et al. . |
| 4,756,709 | 7/1988 | Stevens . |
| 4,790,838 | 12/1988 | Pigneul et al. . |
| 4,795,455 | 1/1989 | Luceri et al. . |
| 4,834,739 | 5/1989 | Linker et al. . |
| 4,857,067 | 8/1989 | Wood et al. . |
| 4,900,319 | 2/1990 | Richwine . |
| 4,900,320 | 2/1990 | McCoy . |
| 4,911,701 | 3/1990 | Mavinkurve . |
| 4,917,697 | 4/1990 | Osborn, III et al. . |
| 4,936,839 | 6/1990 | Molee et al. . |
| 4,940,462 | 7/1990 | Salerno . |
| 4,944,735 | 7/1990 | Mokry . |
| 5,037,417 | 8/1991 | Ternstrom et al. . |
| 5,080,658 | 1/1992 | Igaue et al. . |
| 5,087,254 | 2/1992 | Davis et al. . |
| 5,129,893 | 7/1992 | Thoren . |

(List continued on next page.)

FOREIGN PATENT DOCUMENTS

| | | |
|---|---|---|
| 79205822 | 4/1989 | China . |
| 0 249 924 | 12/1987 | European Pat. Off. . |
| 0 335 527 | 4/1989 | European Pat. Off. . |
| 0 330 206 A1 | 8/1989 | European Pat. Off. . |
| 0 331 018 A1 | 9/1989 | European Pat. Off. . |
| 0 405 403 A2 | 1/1991 | European Pat. Off. . |
| 0 426 235 A2 | 5/1991 | European Pat. Off. . |
| 0 464 855 A1 | 1/1992 | European Pat. Off. . |
| 0 467 184 A1 | 1/1992 | European Pat. Off. . |
| 0 471 587 A1 | 2/1992 | European Pat. Off. . |
| 0 511 905 A1 | 11/1992 | European Pat. Off. . |
| 563-180031 | 11/1988 | Japan . |
| H3-46316 | 8/1991 | Japan . |
| H4-126145 | 4/1992 | Japan . |
| H5-24026 | 3/1993 | Japan . |
| H5-95975 | 4/1993 | Japan . |
| WO 92/18080 | 10/1992 | WIPO . |

*Primary Examiner*—John G. Weiss
*Assistant Examiner*—Dennis Ruhl
*Attorney, Agent, or Firm*—Jeffrey V. Bamber; Steven W. Miller; Jacobus C. Rasser

[57] ABSTRACT

An absorbent article such as a sanitary napkin, having flaps and a recessed area wherein the flaps may be tucked.

8 Claims, 12 Drawing Sheets

U.S. PATENT DOCUMENTS

| | | |
|---|---|---|
| 5,133,705 | 7/1992 | Nakanishi et al. . |
| 5,221,275 | 6/1993 | Van Iten . |
| 5,281,209 | 1/1994 | Osborn, III et al. ................ 604/385.1 |
| 5,330,461 | 7/1994 | Leeker . |
| 5,344,416 | 9/1994 | Niihara . |
| 5,346,486 | 9/1994 | Osborn et al. . |
| 5,354,400 | 10/1994 | Lavash et al. . |
| 5,389,094 | 2/1995 | Lavash et al. . |
| 5,472,437 | 12/1995 | Akiyama et al. . |
| 5,520,676 | 5/1996 | Lavash et al. . |

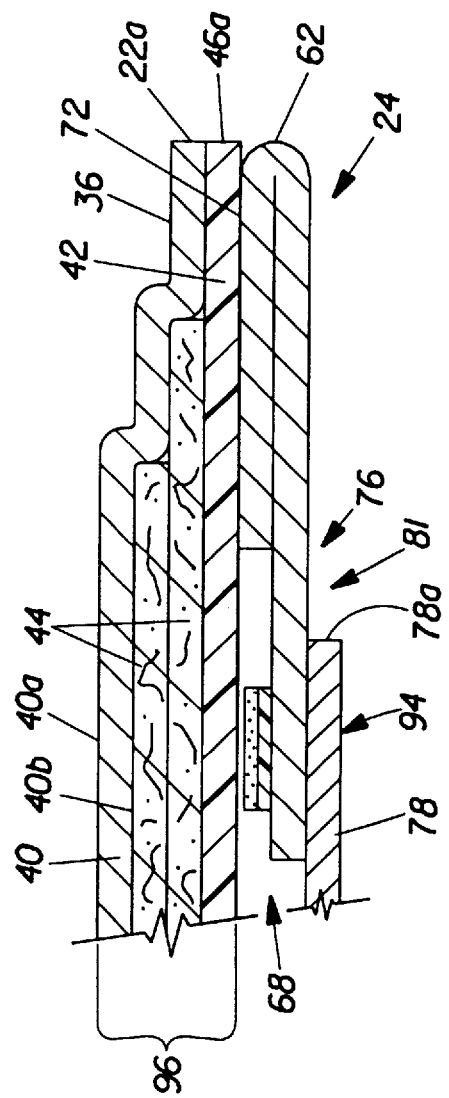

ABSORBENT ARTICLE HAVING TUCKED FLAPS

This is a continuation of application Ser. No. 08/632,733, filed on Apr. 15, 1996, now abandoned, which was a continuation of application Ser. No. 08/134,325, filed on Oct. 7, 1993, (now abandoned), which was a continuation of application Ser. No. 07/906,629, filed on Jun. 30, 1992 (now U.S. Pat. No. 5,281,209).

FIELD OF THE INVENTION

The present invention relates to disposable absorbent articles such as sanitary napkins, adult incontinence devices, and the like. Still more particularly, the present invention concerns such disposable absorbent articles having side flaps.

BACKGROUND OF THE INVENTION

All manner and variety of absorbent articles configured for the absorption of body fluids such as menses, urine, and feces are, of course, well known. Absorbent articles, particularly sanitary napkins, having wings or flaps are disclosed in the literature and are available in the marketplace.

Generally, the flaps extend laterally from a central absorbent means and are intended to be folded around the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties.

The flaps serve at least two purposes. First, the flaps prevent exudates which otherwise would soil the edges of the wearer's panties from doing such. Second, the flaps help stabilize the napkin from shifting out of place, especially when the flaps are affixed to the underside of the panties.

Sanitary napkins having flaps of the various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957.

While flaps greatly improve the effectiveness of a sanitary napkin, the flaps of a sanitary napkin may hinder or impede application of the sanitary napkin to the crotch of the wearer's panty. Currently, each of the flaps of a sanitary napkin have an end, the distal end, which may move freely relative to the sanitary napkin. Once the release paper of the central pad adhesive is removed by the wearer, the distal ends of the flaps may fall between the crotch portion of the wearer's panty and the sanitary napkin and may become adhered to the central pad adhesive. Therefore, there is a need for a sanitary napkin having flaps positioned so that they will not interfere with the application of the sanitary napkin to the panty.

Currently, sanitary napkins having flaps will not function properly unless the flaps are used (i.e, are folded down along the edges of the crotch of the wearer's undergarment and affixed to the underside of the undergarment). Generally, as they are packaged, the flaps of a sanitary napkin are folded over the garment side of the sanitary napkin or are folded over the body-facing side of the sanitary napkin. Therefore, if the flaps are not used while the sanitary napkin is being used, the flaps will either obstruct the surface intended to receive bodily exudates on the body-facing side of the sanitary napkin, or will obstruct the adhesive or other fastening means positioned on the garment side of the sanitary napkin. While sanitary napkins having flaps are commonly viewed as providing better protection against soiling as compared to sanitary napkins without flaps, some women still prefer a sanitary napkin without flaps, and some women who generally prefer a sanitary napkin with flaps, occasionally (such as during periods of light flow) prefer a sanitary napkin without flaps. Therefore, there is a need for a sanitary napkin having flaps which may or may not be used while the sanitary napkin is being used.

Accordingly, it is an object of the present invention to provide an absorbent article, such as a sanitary napkin, having tucked side flaps, i.e., flaps which are tucked in a recessed area, which will not impede or hinder application of the absorbent article to the crotch of the wearer's panty.

It is also an object of the present invention to provide an absorbent article, such as a sanitary napkin, having optional side flaps, i.e., flaps which are tucked into a recessed area and which may or may not be used while the absorbent article is being used.

It is an additional object of the present invention to provide an absorbent article having tucked side flaps and zones of differential extensibility for relieving the stresses that develop in the flaps when they are folded down along the edges of the crotch of the wearer's undergarments and affixed to the underside of the undergarments.

These and other objects of the present invention will be more readily apparent when considered in reference to the following description and when taken in conjunction with the accompanying drawings.

SUMMARY OF THE INVENTION

In accordance with the present invention, an absorbent article, such as a sanitary napkin, having tucked side flaps is provided.

The sanitary napkin has a main body portion and a pair of flaps joined to the main body portion at a line of juncture. The main body portion comprises an absorbent assembly and a pair of retaining members joined to the absorbent assembly to form a pair of recessed areas. The absorbent assembly comprises an absorbent core and two spaced apart longitudinal edges. Each of the retaining members comprise two end regions, a center region positioned between and joined to the end regions, and a longitudinal edge. At least a portion of each of the end regions is joined to the absorbent assembly at a point of connection, and at least a portion of the center region is decoupled from the absorbent assembly to form a recessed area. Each of the flaps has a proximal edge adjacent the line of juncture and a distal edge disposed away from the line of juncture. A portion of one of the flaps is capable of being tucked into one of the recessed areas and a portion of the other flap is capable of being tucked into the other recessed area.

In a particularly preferred embodiment of the sanitary napkin, the flaps will have zones of differential extensibility which provide a means for the relief of stresses in the flaps when the sanitary napkin is placed in the wearer's undergarments.

BRIEF DESCRIPTION OF THE DRAWINGS

FIG. 1a is a lateral cross-sectional view taken along line a—a of FIG. 1 through one of the flaps of the sanitary napkin along section line 1a—1a.

FIG. 5a is a sectional view of one of the flaps of the sanitary napkin of FIG. 5 taken along section line 5a—5a.

FIG. 6a is a sectional view of the tucked flap of the sanitary napkin of FIG. 6 taken along section line 6a—6a.

FIG. 7 is a view of another sanitary napkin embodiment taken from an angle similar to that of FIG. 2a.

DETAILED DESCRIPTION OF PREFERRED EMBODIMENTS

1. Introduction

A. The Absorbent Article In General

Figure 1:
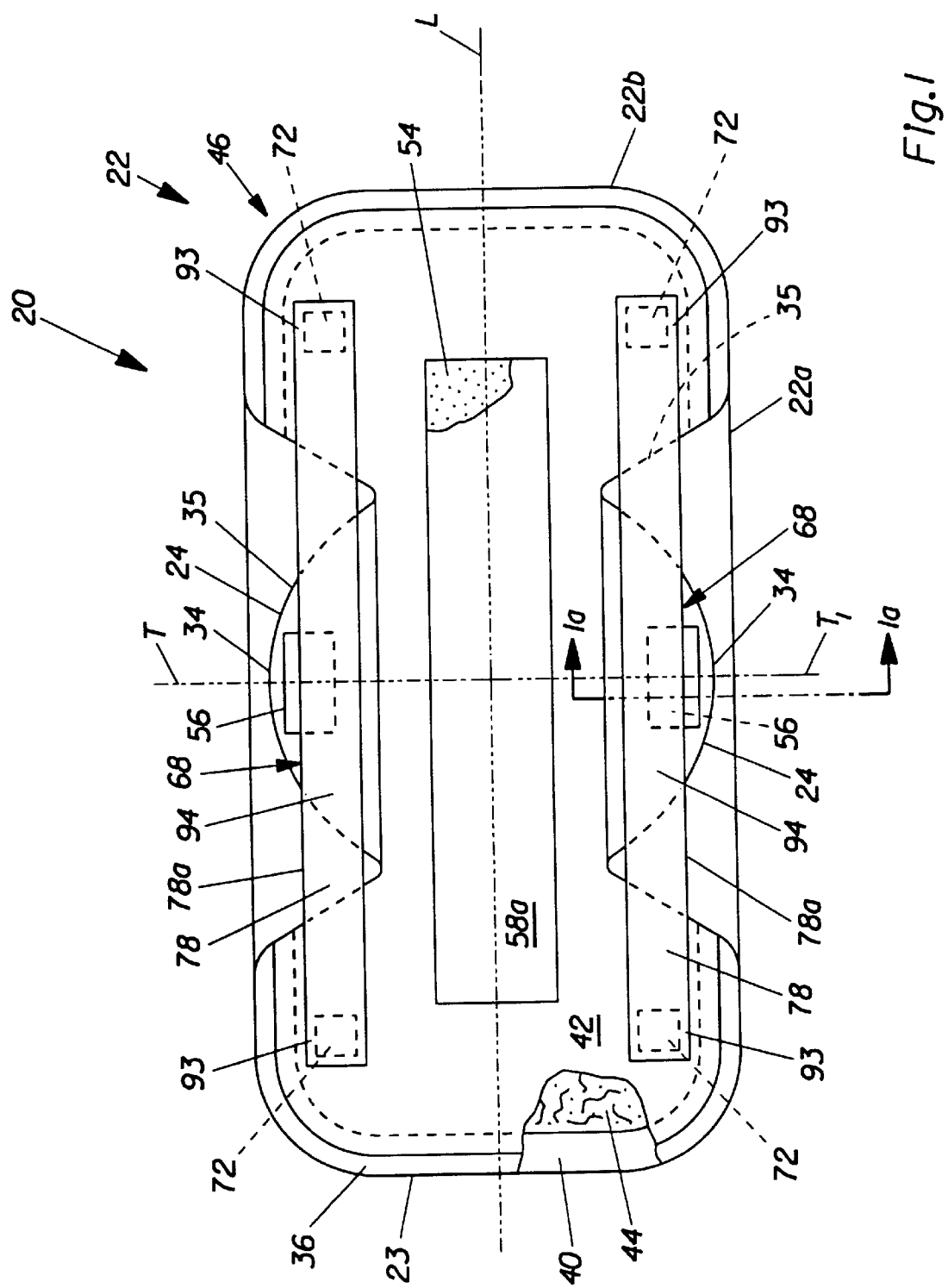
FIG. 1 is a top plan view of a sanitary napkin embodiment of the present invention with the garment side facing the viewer and the flaps tucked in the recessed areas.

The present invention relates to disposable absorbent articles, such as sanitary napkins. More particularly, the present invention relates to such disposable absorbent articles having flaps that are folded down along the edges of the crotch of the wearer's undergarments and attached to the underside of the undergarments.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinent pads (and other articles worn in the crotch region of a garment). The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) As used herein the terms "optional flaps" or "tucked flaps" shall refer to the flaps of an absorbent article, which are tucked into a recessed area, or are capable of being tucked into a recessed area. A flap is capable of being tucked into a recessed area if it is joined to the sanitary napkin such that at least a portion of the flap may be positioned between the decoupled portion of a retaining member and the absorbent assembly of the main body portion. In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

A preferred embodiment of a sanitary napkin 20 of the present invention is shown in FIG. 1. As shown in FIG. 1, the sanitary napkin 20 basically comprises a main body portion 22 and two flaps 24 (shown in the tucked position) joined to the main body portion 22. The main body portion 22 comprises an absorbent means represented by an absorbent assembly 46 and two retaining members 78 joined to the absorbent assembly 46. (In the discussion that follows, unless otherwise noted, the sanitary napkin described herein will have two retaining members. While it is not necessary that the sanitary napkin have two retaining members, two retaining members are preferred over one retaining member. Also, while it is not necessary that the retaining members be mirror images of one another, they preferably are. Thus, the description of one retaining member will be a description of the other, and, for clarity, discussion of the second retaining member may be omitted.)

As used herein, the term "joined" encompasses configurations whereby an element is directly secured to the other element by affixing the element directly to the other element; configurations whereby the element is indirectly secured to the other element by affixing the element to intermediate member(s) which in turn are affixed to the other element; and configurations whereby one element is integral with another element, i.e., one element is essentially part of the other element.

The retaining member 78 comprises a pair of end regions 93 and a center region 94 positioned between and joined to the end regions 93. At least a portion of the end regions 93 are joined to the absorbent assembly 46. At least a portion of the center region 94 is detached or decoupled from the absorbent assembly 46. The area between the decoupled center region 94 and the absorbent assembly 46, forms a recessed area 68 wherein a portion of at least one of the flaps 24 may be tucked. The end regions 93 are each joined to the absorbent assembly 46 at a point of connection 72. As used herein, the term "point of connection" refers to regions where the retaining member 78 is joined to the absorbent assembly 46 of the main body portion 22. These regions can be of any shape or configuration, but they are not limited to spots or points. Thus, these regions can comprise flanges, strips, intermittent lines, spots, and the like. In the embodiment illustrated in FIG. 1, each point of connection 72 comprises a single rectangular bond site.

The absorbent assembly 46 preferably comprises a liquid pervious topsheet 40, a liquid impervious backsheet 42 joined to the topsheet 40, and an absorbent core 44 positioned between the topsheet 40 and the backsheet 42.

Figure 1A:
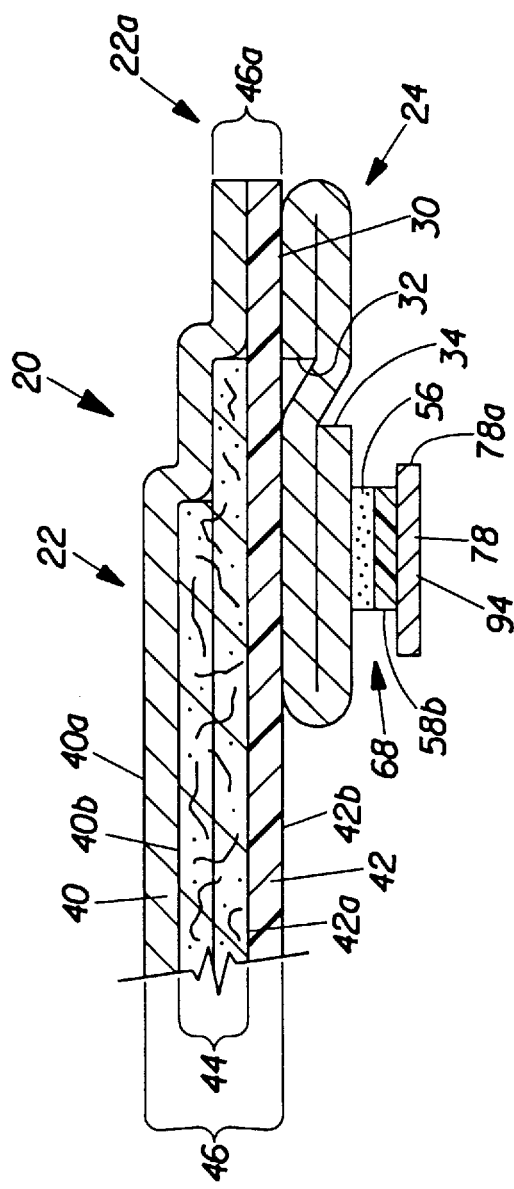

Both of the flaps 24 shown in FIGS. 1 and 1a are formed from a discrete piece of material which is attached to the absorbent assembly 46 of the main body portion 22. (In alternative embodiments, such as those shown in U.S. Pat. No. 4,917,697 issued to Osborn, the flaps 24 may be integral with the absorbent assembly 46 of the main body portion 22. In such a case, the topsheet 40 may form one surface of both the flaps 24 and the main body portion 22, and the backsheet 42 may form the other surface of the same. In addition, the absorbent material of the sanitary napkin 20 may extend into the flaps 24 to form a flap absorbent core, as described in greater detail in U.S. Pat. No. 4,917,697. In other alternative embodiments, each flap may be comprised of a separate piece of material joined to the main body portion 22. Such embodiments are shown in U.S. patent application Ser. No. 07/769,891, "Absorbent Article Having Flaps and Zones of Differential Extensibility", filed Oct. 1, 1991 in the name of Bruce Lavash, et al. and U.S. patent application Ser. No. 07/832,246, "Absorbent Article Having Inwardly-Folded Pleated Flaps", filed Feb. 7, 1992 in the name of Kaoru Niihara and Thomas W. Osborn, III. In other alternative embodiments, each flap may be integral with the retaining member 78 of the main body portion 22.) In the discussion that follows, unless otherwise noted, the sanitary napkin described herein will have two flaps. While it is not necessary that the sanitary napkin have two flaps, two flaps are preferred over one flap. Also, while it is not necessary that the flaps be mirror images of one another, they preferably are. Thus, the description of one flap will be a description of the other, and, for clarity, discussion of the second flap may be omitted.

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

The flaps 24 are each associated with the main body portion 22 along a juncture 30. This is typically a longitudinally-oriented (or "longitudinal") juncture, such as lines of juncture 30. As used herein, the terms "juncture" (or "line of juncture") refer to regions where the flaps 24 extend from or are joined to the main body portion 22. These regions can be any of various curved or straight lines, but they are not limited to lines. Thus, these regions can comprise flanges, strips, intermittent lines, and the like.

The flaps 24 have a proximal edge 32 adjacent the line of juncture. A distal edge (or "free end") 34 is remote from the line of juncture 30. As shown in FIG. 1, each flap 24 is divided into a front half 26, and a back half 28 by a flap transverse centerline $T_1$. The flap transverse centerline $T_1$ may coincide with the principal transverse centerline T of the sanitary napkin, but this is not absolutely required.

A sanitary napkin 20 of the present invention comprises at least one recessed area 68 (preferably two recessed areas) in which the flaps 24 may be tucked. The recessed area 68 is formed between a decoupled portion of the center region 94 of the retaining member 78 and the absorbent assembly 46 of the main body portion 22. The recessed area 68 will be formed by joining the end regions 93 of the retaining member 78 with the absorbent assembly 46 of the main body portion 22 at points of connection 72. The recessed area 68 will have a mouth 76 (shown in FIG. 2a). The mouth 76 is formed between the longitudinal edge 78a of the decoupled portion of the retaining member 78 and the absorbent assembly 46 of the main body portion 22.

2. The Individual Components of the Absorbent Article

The individual components of the main body portion 22 of the sanitary napkin 20 will first be looked at in greater detail.

A. The Absorbent Assembly (1) The Topsheet

The topsheet 40 is liquid permeable and when the sanitary napkin 20 is in use, the topsheet 40 is in close proximity to the skin of the user. The topsheet 40 is compliant, soft feeling, and non-irritating to the user's skin. It can be made from any of the materials conventional for this type of use. Nonlimiting examples of suitable materials that can be used as topsheet 40 are woven and nonwoven polyester, polypropylene, nylon, and rayon and formed thermoplastic films, with formed films being preferred.

Suitable formed films are described in U.S. Pat. No. 3,929,135, entitled "Absorptive Structure Having Tapered Capillaries", which issued to Thompson on Dec. 30, 1975, U.S. Pat. No. 4,324,426, entitled "Disposable Absorbent Article Having A Stain-Resistant Topsheet", which issued to Mullane and Smith on Apr. 13, 1982, U.S. Pat. No. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which issued to Ahr, Louis, Mullane, and Ouellette on Jul. 31, 1984. Formed films are preferred for topsheet 40 because they are pervious to liquids and yet non-absorbent. Thus, the surface of the formed film which is in contact with the body remains dry and is more comfortable to the wearer.

The sanitary napkin 20 may also be comprised of components that are extensible (i.e., capable of stretching, particularly in the longitudinal direction) when the sanitary napkin is worn. The sanitary napkin 20 may capable of elongating between about 15% and about 40% of its unstretched length. This extensibility provides better in-use fit, comfort, and decreased staining. In other embodiments, only limited portions of the components of the sanitary napkin 20 are capable of stretching. Such an embodiment (without the tucked flaps of the present invention) is described in greater detail in co-pending, commonly-assigned U.S. patent application Ser. No. 07/769,891, "Absorbent Article Having Flaps and Zones of Differential Extensibility", filed Oct. 1, 1991, in the name of Bruce Lavash, et al.

A particularly preferred topsheet 40 for use in such an embodiment is one which is made in accordance with U.S. Pat. No. 4,463,045 and ring rolled to provide it with a degree of longitudinal extensibility. Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 entitled "Improved Method And Apparatus For Incrementally Stretching A Zero Strain Stretch Laminate Web To Impart Elasticity Thereto" filed by Gerald M. Weber et al. on Feb. 28, 1991, U.S. patent application Ser. No. 07/662,537 entitled "Improved Method and Apparatus For Incrementally Stretching Zero Strain Stretch Laminate Web In A Non-Uniform Manner To Impart A Varying Degree of Elasticity Thereto" filed by Kenneth B. Buell et al. on Feb. 28, 1991, and U.S. patent application Ser. No. 07/662,543 entitled "Improved Method And Apparatus For Sequentially Stretching Zero Strain Stretch Laminate Web To Impart Elasticity Thereto Without Rupturing The Web" filed by Gerald M. Weber et al. on Feb. 28, 1991. The fold lines in the corrugations of the topsheet should run in the transverse direction so the topsheet is longitudinally extensible.

Such a topsheet is described in greater detail in the following patent applications which were filed on Jun. 23, 1991: U.S. patent application Ser. No. 07/734,404 entitled "Absorbent Articles, Especially Catamenials, Having Improved Fluid Directionality, Comfort and Fit" filed in the names of Thompson, et al.; U.S. patent application Ser. No. 07/734,392 entitled "Fluid Handling Structure for Use in Absorbent Articles" filed in the names of Thompson, et al.; and, U.S. patent application Ser. No. 07/734,405 entitled "Absorbent Core for Use in Catamenial Products" filed in the names of Buenger, et al. These patent applications may be referred to collectively as the "Capillary Channel Fiber" patent applications.

In addition, in preferred embodiments of the present invention, at least a portion of the outer surface 40a of the topsheet 40 is treated with a surfactant. It is preferred that the surfactant be substantially evenly and completely distributed across at least the portion of the outer surface 40a of topsheet 40 that overlays the absorbent assembly 46 of the main body portion 22. This can be accomplished by any of the common techniques well known to those skilled in the art. For example, the surfactant can be applied to topsheet 40 by spraying, by padding, or by the use of transfer rolls.

Treating the outer surface 40a of the topsheet 40 with a surfactant renders the surface of the topsheet 40 more hydrophilic. This results in liquid penetrating the topsheet 40 faster than it would if the surface were not treated. This diminishes the likelihood that menstrual fluids will flow off topsheet 40 rather than being absorbed by the absorbent core 44. Preferably, any portions of the topsheet 40 that overlay the flaps 24 are not treated with the surfactant. This will minimize any tendencies fluids may have to spread laterally across the flaps and to come in contact with the wearer's thighs and other parts of the wearer's body.

In preferred embodiments, the inner surface 40b of topsheet 40 is secured in contacting relation with the absorbent core 44. This contacting relationship results in liquid penetrating topsheet 40 faster than if the topsheet 40 were not in contact with absorbent core 44. The topsheet 40 can be maintained in contact with absorbent core 44 by applying adhesive to the inner surface 40b of the topsheet 40. Suitable adhesives useful for this purpose are described in U.S. Pat. No. 4,917,697. The adhesives can be applied by the same methods as the surfactant is applied to the outer surface 40a of the topsheet 40.

The retaining member 78 may be formed from the topsheet 40 or from a portion of the topsheet 40. However, it is preferred that the retaining member be formed from a portion of the flaps 24, a portion of the backsheet 42, or from a discrete piece of material.

(2) The Absorbent Core

The absorbent core 44 is positioned between the topsheet 40 and the backsheet 42. The absorbent core 44 provides the means for absorbing menstrual fluid. The absorbent core 44 need not have an absorbent capacity much greater than the total amount of menstrual fluid anticipated to be absorbed. The absorbent core 44 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibers, polymeric fibers, hydrogel-forming polymer gelling agents, peat moss, or any equivalent material or combinations of materials.

Polymeric gelling agents are those materials which, upon contact with fluids (i.e., liquids) such as water or body fluids, imbibe such fluids and thereby form hydrogels. In this manner, fluids discharged into the absorbent core 44 can be acquired and held by the polymeric gelling agent, thereby providing the articles herein with enhanced absorbent capacity and/or improved fluid retention performance.

The polymeric gelling agent which is employed in the absorbent core 44 will generally comprise particles of a substantially water-insoluble, slightly cross-linked, partially neutralized, hydrogel-forming polymer material. The term "particles", as used herein, can refer to particles in any form, such as in the form of pellets, flakes, or fibers. The characteristics of the absorbent core 44 (including, but not limited to the preferred types of polymer materials used therein, and types of methods which can be used for preparing these polymer particles) are described in greater detail in U.S. Pat. No. 5,009,653 issued to Osborn and the patents incorporated by reference in that patent, the disclosures of which are all incorporated by reference herein.

In one preferred embodiment, the absorbent core 44 is a laminate comprised of a layer of superabsorbent polymer material, such as in the form of particles, disposed between two air-laid tissues, first and second tissue layers (or "upper" and "lower" tissue layers). The first and second tissue layers provide containment of the superabsorbent polymer material, improve lateral wicking of the absorbed exudates throughout the absorbent core 44 and provide a degree of absorbency.

A suitable laminate is the superabsorbent laminate WATER-LOCK L-535 available from the Grain Processing Corporation of Muscatine, Iowa (WATER-LOCK registered ™ by Grain Processing Corporation). Such superabsorbent laminates are disclosed in U.S. Pat. No. 4,467,012, entitled "Composition For Absorbent Film And Method Of Preparation", which issued to Pedersen et al. on Aug. 21, 1984, and U.S. Pat. No. 4,260,443, entitled "Laminated Absorbent Process", which issued to Lindsay et al. on Apr. 7, 1981.

The absorbent core 44 may be a laminate, as described above, which is slitted or partially slitted for longitudinal extensibility. This slitted or partially slitted core is described in greater detail in the Capillary Channel Fiber patent applications.

(3) The Backsheet

The backsheet 42 is impervious to liquids and, thus, prevents menstrual fluid from soiling the clothing of the user. Any material used in the art for such purpose can be utilized herein. Suitable materials include embossed or non-embossed polyethylene films and laminated tissue. A suitable polyethylene film is manufactured by Monsanto Chemical Corporation and marketed in the trade as Film No. 8020.

In one alternative embodiment of the sanitary napkin 20 (typically in which the topsheet 40 overlays only the main body portion 22 and does not extend out to form the top surface of the flaps), the backsheet 42 may be comprised of two layers. In such a case, the backsheet 42 may comprise a first layer of lofted material disposed on the core-facing side 42a of the backsheet. The purpose of the first layer is to provide a comfortable, non-irritating surface against the body of the wearer. The lofted layer may be comprised of any suitable material, such as a nonwoven material. Preferably, the lofted layer comprises a hydrophobic nonwoven material. The second layer may be disposed on the garment side 42b of the backsheet 42, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Ethyl Corporation, Visqueen Division, under model XP-39385 has been found particularly well suited for this second layer. The backsheet 42 may also be made of a soft, cloth-like material which is hydrophobic relative to the topsheet 40. A polyester or polyolefinic fiber backsheet 42 has been found to work well. A particularly preferred soft, cloth-like backsheet 42 material is a laminate of a polyester nonwoven material and a film such as described in U.S. Pat. No. 4,476,180 issued to Wnuk on Oct. 9, 1984.

A particularly preferred extensible backsheet 42 is an extended adhesive film Formula #198-338 manufactured by the Findley Adhesives Company of Wauwatosa, Wis. which is described in greater detail in the Capillary Channel Fiber patent applications.

B. The Retaining Member

The main body portion 22 of the sanitary napkin 20 will have at least one retaining member 78 joined to the absorbent assembly 46. Each of the end regions 93 of the retaining member 78 will be joined to the absorbent assembly at a point of connection 72, and at least a portion of the center region 94 of the retaining member 78 will be detached or decoupled from the absorbent assembly 46. A recessed area 68 is formed between the decoupled portion of the center region 94 of the retaining member 78 and the absorbent assembly 46.

The retaining member 78 can be joined to the absorbent assembly 46 of the main body portion 22 in a number of different manners. Many of the different ways a component (such as the retaining member 78) can be "joined to" or "associated with", etc. another component are set forth in the definitions of these terms contained in U.S. Pat. No. 5,007,906 entitled "Decoupled Sanitary Napkin" which issued to Osborn, et al. on Apr. 16, 1991. When the retaining member is comprised of an element discrete from the absorbent assembly 46, i.e. is not integral with the topsheet, backsheet, etc, it can be joined to the absorbent assembly 46 by any techniques known to those skilled in the art. Such techniques include, but are not limited to adhesives, heat and/or pressure, ultrasonics, etc. The point of connection 72 of the end regions 93, are not limited to points or spots and may comprise flanges, strips, intermittent lines, spots, and the like, or may comprise combinations of flanges, strips, intermittent lines, spots, and the like. Therefore, the point of connection 72 may be a line which is concave, straight, or convex and may form any angle relative to the principal longitudinal centerline L.

The retaining members 78 can each be joined to the absorbent assembly 46 of the main body portion 22 along the principal longitudinal centerline L, or along the longitudinal edges 46a of the absorbent assembly 46, or at any place between the principal longitudinal centerline L and the longitudinal edges 46a of the absorbent assembly 46. The retaining members 78 will, of course, generally be on opposite sides of the principal longitudinal centerline L.

The retaining member 78 is generally longitudinally oriented on the absorbent assembly 46. The retaining member is longitudinally oriented on the absorbent assembly 46 when the longitudinal edge 78a of the retaining member 78 is oriented in a direction substantially parallel to the longitudinal centerline L or in a direction having a vector component substantially parallel to the longitudinal centerline L.

The retaining member 78 is generally compliant, soft feeling and non-irritating to the users skin. The retaining member 78 is preferably made from any of the materials conventionally used for sanitary napkins 20. Examples of suitable materials that can be used for the retaining member 78 are woven and nonwoven polyester, polypropylene, nylon, and polyethylene, as well as plastic films. The retaining member 78 may be comprised of one or more of the elements of the absorbent assembly 46, e.g., topsheet 40, backsheet 42, etc. Preferably, the retaining member 78 will comprise a piece of material discrete from the topsheet, backsheet, etc.

The overall size and shape of the retaining members 78 may be readily selected by those skilled in the art and will be dependent upon the desired size and shape of the recessed area 68 and the size and shape of the flaps 24 as they are tucked into the recessed area 68. Although it is not necessary that the retaining members 78 be mirror images of each other, it is preferred that the retaining members 78 are mirror images of each another. Whether or not the retaining members 78 are symmetrical about the principal transverse centerline T is also dependent upon the desired size and shape of the recessed area 68, as well as the location and symmetry of the flaps 24. However, it should be understood that the retaining members 78 need not have a shape, size, or location which exactly corresponds to the size, shape, and location of the flaps 24. It is only required that the retaining members 78 be sized, shaped, and positioned such that the retaining member 78 forms a recessed area 68 which can accommodate the flap 24 in a tucked configuration.

The recessed area 68 may be much smaller in size and shape than the flaps 24. For example, although the size and shape of the recessed areas 68 of FIG. 1 are smaller in size and shape than the flaps 24, it can be seen from FIGS. 1 and 1a that the recessed areas 68 are sufficient in size and shape to accommodate the flaps 24 in their tucked configuration.

It is not necessary that each retaining member 78 be formed of a separate piece of material as shown in FIGS. 1 and 1a. Each retaining member 78 may each be formed from the same piece of material. It is also not necessary that the retaining members 78 be joined to the backsheet 42 of the absorbent assembly 46. The retaining members 78 may be joined to any element of the absorbent assembly 46. Many various configurations of a sanitary napkin 20 having a retaining member 78 joined thereto to form a recessed area 68, will be readily apparent to one skilled in the art.

3. Assembly of Components into a Sanitary Napkin, Formation of Flaps, and Function of the Sanitary Napkin A. Assembly of Components As shown in FIGS. 1 and 1a, the topsheet 40 is secured to backsheet 42 along a first seam, such as seam 36. The seam 36 can be formed by any means commonly used in the art for this purpose such as by gluing, crimping, or heat-sealing. The seam 36 is illustrated in FIG. 1 as extending completely around the periphery 23 of the absorbent assembly 46 of the main body portion 22. This is a preferred embodiment for ease of construction. (Other means of uniting the various elements can be used.)

The absorbent assembly 46 is the portion of the main body portion 22 that contains an absorbent means, such as absorbent core 44. The absorbent assembly 46 of the main body portion 22 has a liquid pervious body contacting surface (represented in FIG. 1a by topsheet 40) and an opposed liquid impervious surface (represented in FIG. 1a by backsheet 42). It is to be understood that the embodiment illustrated is only one possible embodiment, albeit a preferred one. Other possible embodiments include one in which an absorbent core 44 is essentially completely wrapped with topsheet before it is placed on a backsheet. The absorbent assembly 46 of the main body portion 22 can also comprise an absorbent core which possesses sufficient integrity to stand alone and is liquid pervious on one surface while the other surface has been treated to render it liquid impervious.

The absorbent assembly 46 of the main body portion 22 may be relatively thick or relatively narrow and thin. A narrow absorbent assembly 46 may be effective because the overall configuration and use of sanitary napkin 20 results in absorbent assembly 46 of the main body portion 22 being maintained in close proximity to the body. Such proximity of the absorbent assembly 46 places it precisely where it should be: very near the body at the vaginal opening. The absorbent assembly 46 of the main body portion 22 can then absorb the vast majority of the menstrual fluid (menses) before it has an opportunity to flow along the sides of the main body portion 22. A thin absorbent assembly may also be desired because it is typically comfortable to the user.

FIGS. 1 and 1a also show the pad securement member, central pad adhesive 54, and the flap securement member, flap adhesive 56, which are adapted to secure the sanitary napkin 20 to the crotch region of an undergarment.

Although the pad securement member is described herein as a central pad adhesive 54 and the flap securement member is described herein as a flap adhesive 56, it should be understood that fastening means other than adhesives can be used as the pad securement member and the flap securement member. Any type of fastener or combination of fasteners used in the art can be used for such a purpose. For example, the sanitary napkin 20 could be secured to the wearer's undergarment by the fastener described in U.S. Pat. No. 4,946,527 entitled "Pressure-Sensitive Adhesive Fastener and Method of Making the Same" issued to Battrell on Aug. 7, 1990. Other examples of fastening means would include mechanical fasteners such as those which are well known in the art. Particularly preferred mechanical fasteners are disclosed in commonly-assigned, co-pending, U.S. patent application Ser. No. 07/718,727, "Screen Printing Method for Manufacturing a Refastenable Mechanical Fastening System and Fastening System Produced Therefrom", filed Jun. 21, 1991, in the name of Dennis A. Thomas and David J. K. Goulait, and commonly-assigned, co-pending, U.S. patent application Ser. No. 07/719,211, "Method for Manufacturing a Refastenable Mechanical Fastening System Having Azimuthally Angled Prongs and Fastening System Produced Therefrom", filed Jun. 21, 1991, in the name of Dennis A. Thomas and David J. K. Goulait, which patent applications are incorporated herein by reference. For simplicity, however, the pad securement member and the flap securement members will be described in terms of adhesive attachment means, i.e., central pad adhesive 54 and flap adhesive 56.

The central pad adhesive 54 provides an adhesive attachment means for securing main body portion 22 in the crotch portion of a panty. The outer surface of flap 24, adjacent the distal edge 34 of the flap, is preferably coated with a flap adhesive 56. The flap adhesive 56 is used to assist in maintaining the flap 24 in position after it is wrapped around the edge of the crotch portion of the panty as described below. The flaps 24 can be maintained in position by attaching the flaps 24 to the undergarment, or to the opposing flap. Suitable adhesive fasteners are described in greater detail in U.S. Pat. No. 4,917,697.

The adhesive attachment means are respectively covered by removable release liners, central pad release liner 58a and flap release liner 58b. The pressure-sensitive adhesives should be covered with release liners to protect the adhesives from dirt, to keep the adhesives from drying out, and to keep the adhesives from sticking to extraneous surfaces prior to use. Suitable release liners are described in U.S. Pat. No. 4,917,697.

While a preferred sanitary napkin embodiment of the present invention has been described, numerous other sanitary napkin embodiments having flaps are available and are disclosed in the literature. These could be provided with the tucked flaps of the present invention. In particular, sanitary napkins having flaps are disclosed in U.S. patent application Ser. No. 07/707,233 entitled "Sanitary Napkin Having Laterally Extensible Means for Attachment to the Undergarment of the Wearer", filed May 21, 1991 in the name of Osborn, et al.; U.S. Pat. Nos. 5,009,653 and 4,950,264, both entitled "Thin, Flexible Sanitary Napkin" which issued to Osborn on Apr. 23, 1991 and Aug. 21, 1990, respectively, U.S. Pat. No. 4,940,462, entitled "Sanitary Napkin With Expandable Flaps" which issued to Salerno on Jul. 10, 1990, U.S. Pat. No. 4,917,697 entitled "Sanitary Napkin Having Flaps and Stress Relief Means" which issued to Osborn, III, et al. on Apr. 17, 1990, U.S. Pat. 4,911,701, entitled "Sanitary Napkin Having Elastic Shaping Means" which issued to Mavinkurve on Mar. 27, 1990, U.S. Pat. No. 4,900,320, entitled "Sanitary Napkin With Panty Gathering Flaps" which issued to McCoy on Feb. 13, 1990, U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,241, entitled "Sanitary Napkin", which issued to Clark on Apr. 2, 1957.

Suitable absorbent articles in the form of pantiliners are disclosed in U.S. Pat. No. 4,738,676 entitled "Pantiliner" issued to Osborn on Apr. 19, 1988. Suitable absorbent articles, at least some of which are in the form of adult incontinence products, are described in U.S. patent application Ser. No. 07/637,571 entitled "Absorbent Article Having Rapid Acquiring Wrapped Multiple Layer Absorbent Body" filed by Barry R. Feist, et al. on Jan. 3, 1991.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

B. Side Flaps

The characteristics of the flaps 24 will now be looked at in greater detail. The general construction of flaps 24 suitable for use in the present invention is described in greater detail in the patents and patent applications incorporated by reference herein, such as U.S. Pat. No. 4,917,697 issued to Osborn; U.S. patent application Ser. No. 07/769,891, "Absorbent Article Having Flaps and Zones of Differential Extensibility", filed Oct. 1, 1991 in the name of Bruce Lavash, et al.; and U.S. patent application Ser. No. 07/832,246, "Absorbent Article Having Inwardly-Folded Pleated Flaps", filed Feb. 7, 1992 in the name of Kaoru Niihara and Thomas W. Osborn, III.

The overall size of the flaps 24 can be readily selected by those skilled in the art. Preferably, the flaps 24 are sized so that the sanitary napkin 20 is from about 10 to about 23 centimeters wide between the distal edges 34 of the flaps at their greatest separation. Preferably each flap 24 is from about 5 to at least about 19 centimeters long in the direction parallel to the principal longitudinal centerline L of the sanitary napkin. However, the flap 24 may be as small as 0.5 centimeters long in the direction parallel to the principal longitudinal centerline L of the sanitary napkin 20.

The shape of the flaps 24 can be selected by those skilled in the art. Preferably, not only are the flaps 24 mirror images of each other, the two halves of each flap 26 and 28 are also symmetrical about the flap transverse centerline $T_1$. (It should be understood that the shape and orientation of the flaps described herein are those of a preferred embodiment. They are not mandatory design features.)

Figure 3:
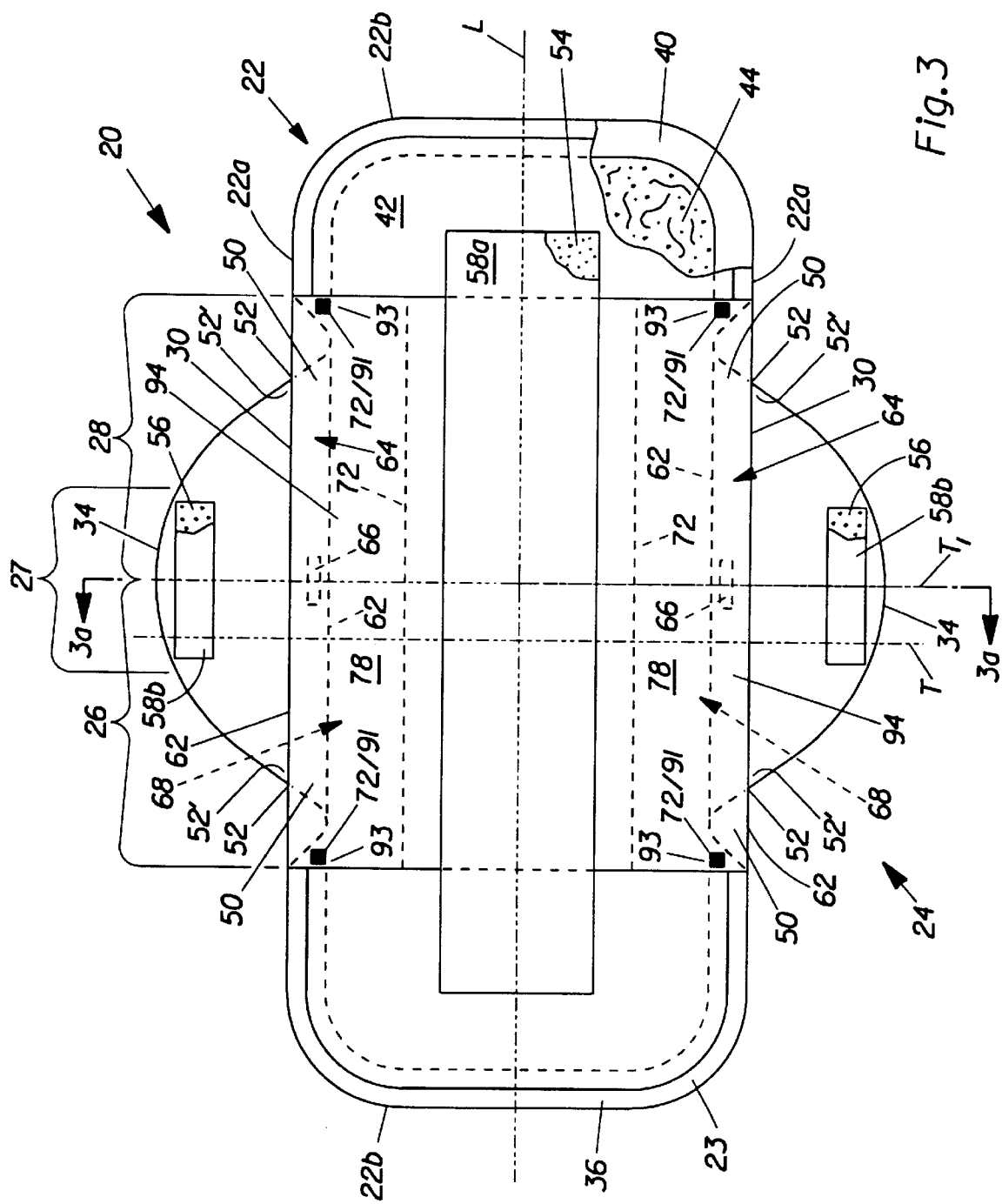
FIG. 3 is a plan view of a sanitary napkin embodiment of the present invention with the garment side facing the viewer and the flaps extended.

Preferably, as in the sanitary napkin 20 illustrated in FIG. 3, the flaps 24 are positioned slightly forward of the principal transverse centerline T of the sanitary napkin. (In such a case, the flap transverse centerline $T_1$ does not coincide with the principal transverse centerline T of the sanitary napkin 20.) The flaps 24, however, are preferably evenly spaced from the principal longitudinal centerline L of the sanitary napkin.

The flaps 24 can be associated with the main body portion 22 in a number of different manners. Many of the different ways a component (such as the flaps 24) can be "joined to" or "associated with", etc. another component are set forth in the definitions of these terms contained in U.S. Pat. No. 5,007,906 entitled "Decoupled Sanitary Napkin" which issued to Osborn, et al. on Apr. 16, 1991. When the flaps comprise separate elements, they can be joined to the main body portion 22 by any techniques known to those skilled in the art. Such techniques include, but are not limited to adhesives, heat and/or pressure, ultrasonics, etc.

Figure 2:
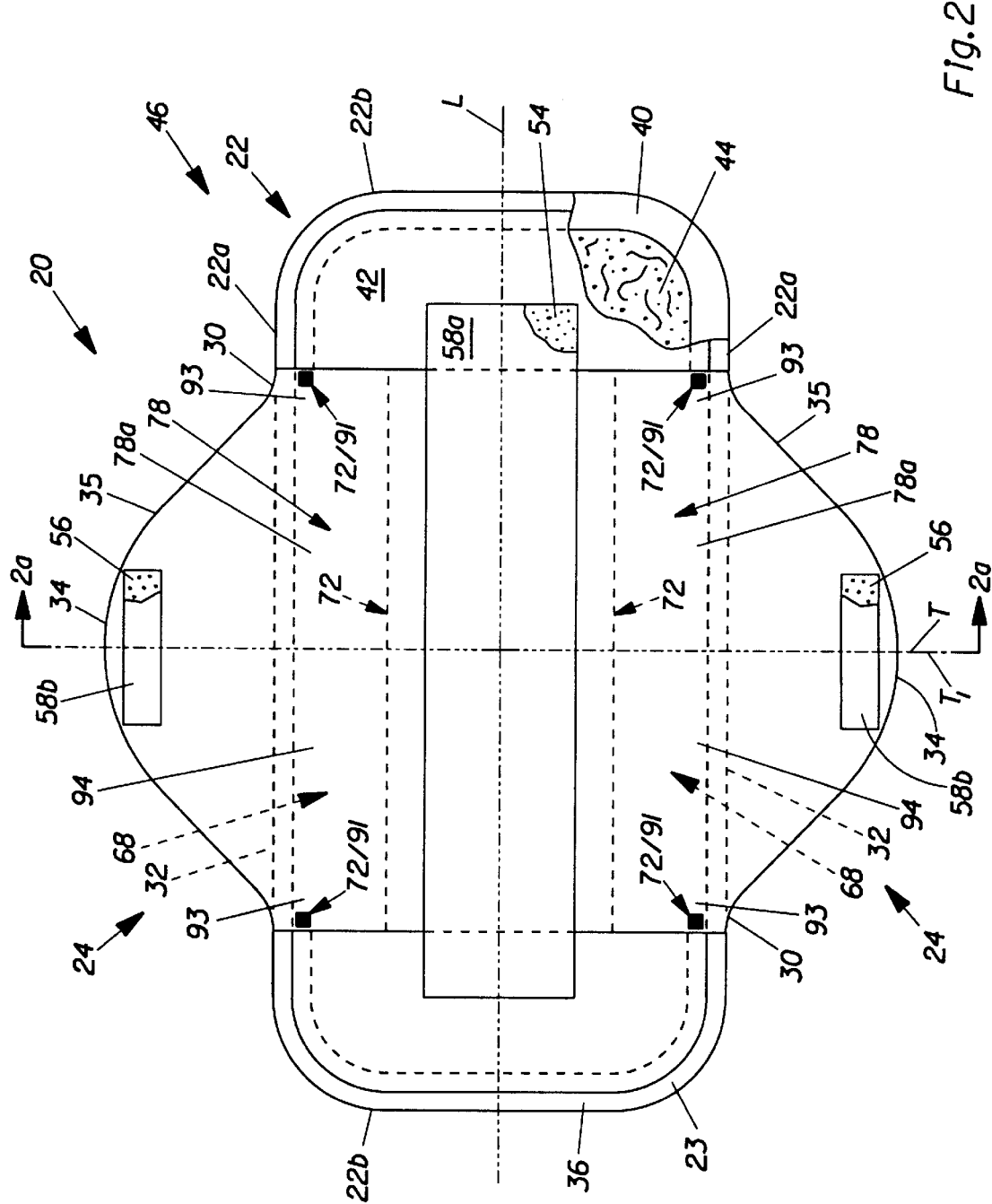
FIG. 2 is a plan view of a sanitary napkin embodiment of the present invention with the garment side facing the viewer and the flaps extended.
Figure 2A:
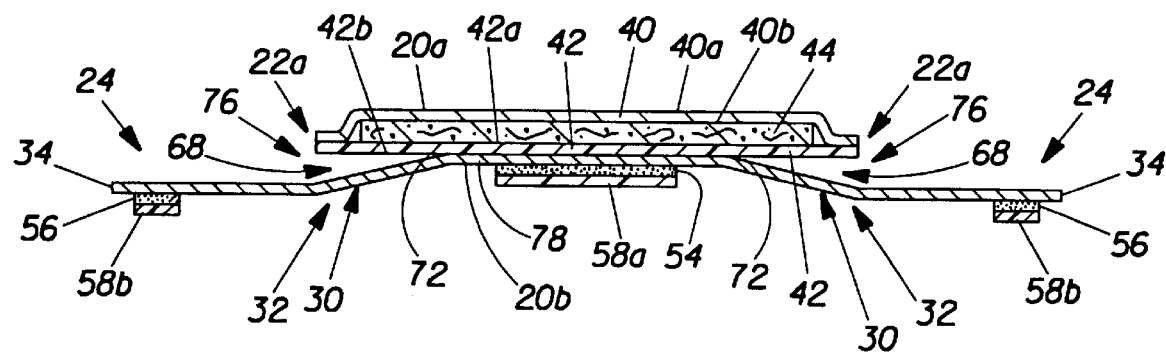
FIG. 2a is a lateral cross-sectional view taken along section line 2a—2a of FIG. 2.

Each flap 24 is joined to the main body portion 22 and is preferably joined to the longitudinal edge 46a of the absorbent assembly 46 or the longitudinal edge 78a of the retaining member 78. In a preferred embodiment, the flap 24 will be joined to the longitudinal edge 78a of the retaining member 78. In a particularly preferred embodiment, as shown in FIGS. 2 and 2a, the flap 24 will be integral with the retaining member 78.

The flaps 24 are joined to the main body portion 22 along lines of juncture 30. The lines of juncture can be concave, straight, (or, but preferably not convex) relative to the principal longitudinal centerline L. The lines of juncture 30 may comprise those lines or areas where separate flap elements are joined to the main body portion 24. Alternatively, when the flaps 24 are integral with the main body portion 22, as in FIGS. 2 and 2a, the lines of juncture 30 may represent lines of demarcation between the main body portion 22 and the flaps 24 (although it is not necessary that there be a precise line of demarcation).

It is not necessary that the flaps 24 extend from (or be joined along) the longitudinal edges 22a of the main body portion 22. The flaps 24 can joined inward (or "inboard") from the longitudinal edges 22a toward the longitudinal centerline such as is shown in U.S. Pat. No. 4,900,320 issued to McCoy on Feb. 13, 1990. The flaps 24 can, thus, each be joined to the main body portion 22 along the principal longitudinal centerline L, or along the longitudinal edges 22a of the main body portion 22, or at any place between the principal longitudinal centerline L and the longitudinal edges 22a of the main body portion 22. The flaps 24 will, of course, generally be on opposite sides of the principal longitudinal centerline L.

C. Function of the Sanitary Napkin and the Recessed Areas

Figure 3A:
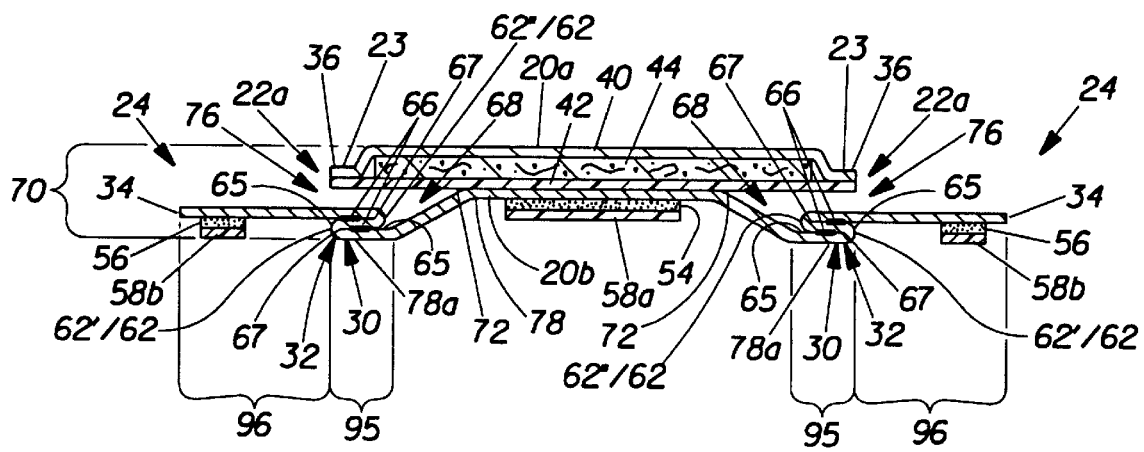
FIG. 3a is a lateral cross-sectional view taken along section line 3a—3a of FIG. 3.
Figure 3B:
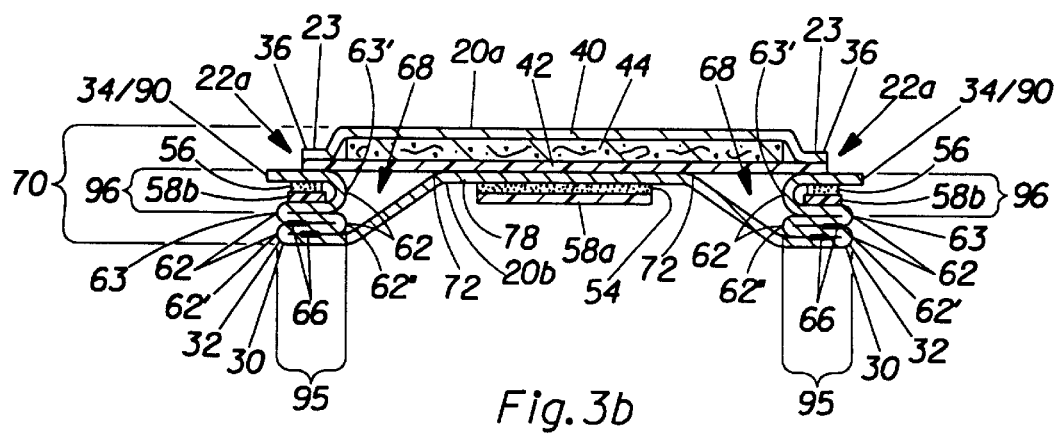
FIG. 3b is a view of the sanitary napkin of FIG. 3a showing the flaps tucked into the recessed areas in a folded configuration.

Preferably each flap 24 will be tucked into a recessed area 68. The tucked flaps 24 may be folded or pleated as shown in FIGS. 3, 3a, and 3b, or corrugated, as shown in FIG. 1 and 1a. Alternatively, the tucked flaps 24 may be non-pleated and non-corrugated, as shown in FIGS. 5, 5a, 6 and 6a.

Figure 2B:
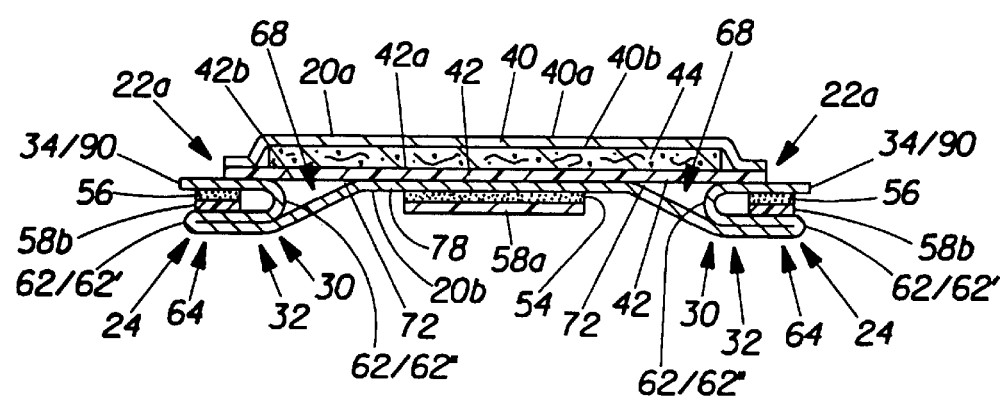
FIG. 2b is a view of the sanitary napkin of FIG. 2a showing the flaps tucked into the recessed areas in a folded configuration.

Referring to FIGS. 2–2b, the sanitary napkin 20 has two recessed areas 68, one on each side of the longitudinal centerline L. It can be seen from FIGS. 2a and 2b that the flaps 24 are integral with the retaining members 78. The retaining members 78 are joined to the absorbent assembly 46 of the main body portion 22 at the points of connection 72. The point of connection 72 of each retaining member 78 comprises a combination of a straight line bond 92 (specifically designated in FIG. 5) and two spot bonds 91. The line bond 92 joins a portion of the center region 94 of the retaining member 78 to the absorbent assembly 46. The two spot bonds 91 join a portion of the end regions to the absorbent assembly 46. The portion of the center region 94 which is decoupled from the absorbent assembly 46 of the main body portion 22 forms the recessed area 68. Although the spot bonds 91 are shown in FIG. 2 as being positioned adjacent to the longitudinal edge 22a of the main body portion 22, the spot bonds 91 may be positioned anywhere between the longitudinal edge 22a of the main body portion 22 and the principal longitudinal centerline L.

It is not necessary that both retaining members 78 be formed of a single piece of material as shown in FIGS. 2, 2a and 2b. Each retaining member 78 may each be formed from a separate piece of material. It is also not necessary that the retaining members 78 be joined to the backsheet 42 of the absorbent assembly 46. The retaining members 78 may be joined to any element of the absorbent assembly 46.

FIG. 2b is a lateral cross-sectional view of the sanitary napkin 20 of FIG. 2 showing the flaps 24 tucked into the recessed areas 68 in a folded configuration. Each flap 24 of the sanitary napkin 20 has a first longitudinal fold 62' which is made upward toward the absorbent assembly 46 and a second fold 62" which is again made upward toward the absorbent assembly 46. This forms a tucked flap 24 which is configured in an S-fold. This configuration allows the distal edge 34 of the flap 24 to form a graspable tab member 90.

Preferably each tucked flap 24 will be provided with a graspable tab member 90. As used herein, the term "tab member" will refer to an element or component of the sanitary napkin 20 which protrudes form the recessed area 68 and may be used to remove the flap 24 from the recessed area 68. The graspable tab member 90 may extend laterally beyond the longitudinal edge 46a of the absorbent assembly 46 or may extend laterally beyond the longitudinal edge 78a of the retaining member 78. Preferably, the graspable tab member 90 extends laterally beyond the longitudinal edges of both the absorbent assembly 46 and the retaining member 78. The graspable tab member 90 preferably extends from the recessed area 68 at least between about 2 millimeters to about 5 millimeters. More preferably, the tab member 90 extends from the recessed area 68 between about 5 millimeters to about 10 millimeters. A preferred tab member 90 is formed by folding, pleating, or corrugating the flap 24 such that the distal edge 34 of the flap 24 protrudes from the mouth 76 of the recessed area 68. There are many different fold configurations which will result in the distal edge 34 of the flap 24 protruding from the mouth 76 of the recessed area 68. An example of particularly preferred fold configurations which results in the distal edge of the flap 24 forming a tab member 90, are shown in FIGS. 2b, 3b, and 7a. Other suitable fold configurations will be readily apparent to those skilled in the art.

Figure 5:
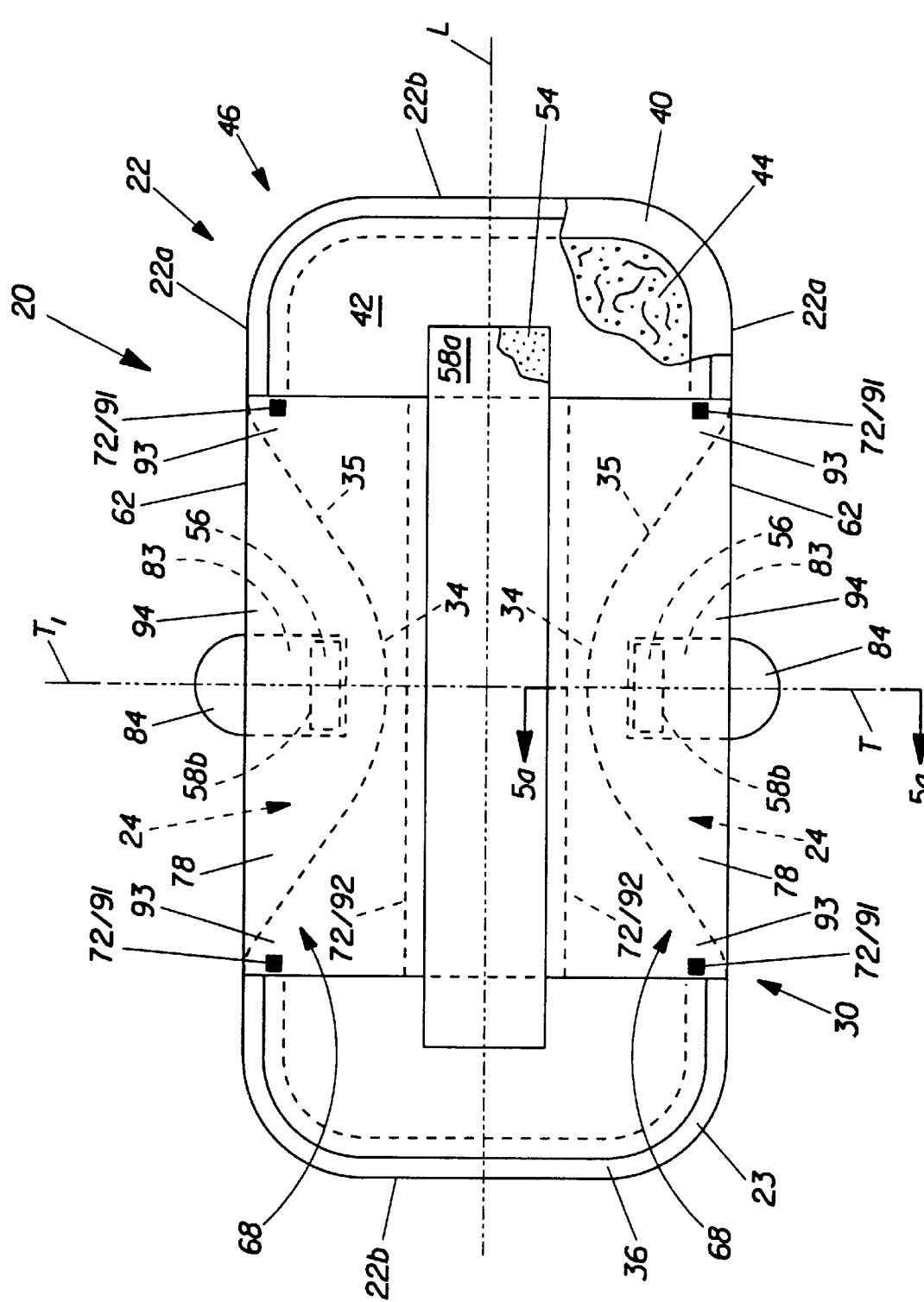
FIG. 5 is a plan view of an alternate sanitary napkin embodiment of the present invention with the garment side facing the viewer.
Figure 5A:
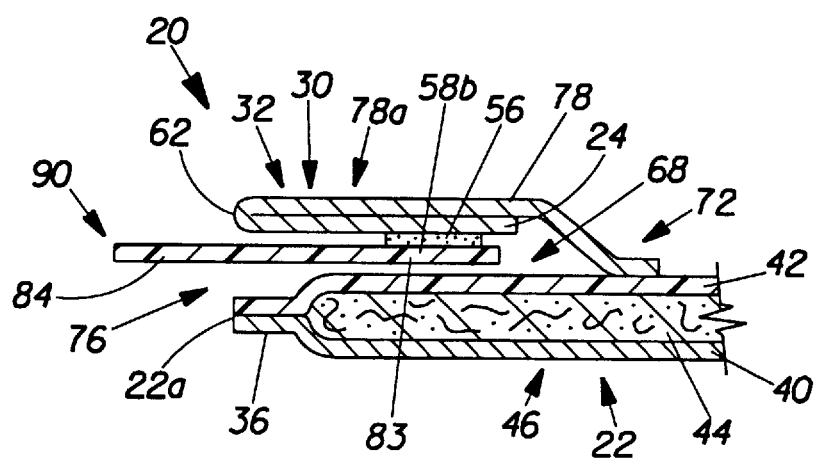

An alternative graspable tab portion is shown in FIGS. 5 and 5a. FIG. 5 is a plan view of a sanitary napkin 20 substantially similar to the sanitary napkin 20 shown in FIG. 2. However, the flaps 24 of the sanitary napkin embodiment of FIGS. 5 and 5a have a different fold configuration than the sanitary napkin of FIG. 2b. The flaps 24, in FIG. 5, are shown tucked into the recessed areas 68 of the main body portion 22, and comprise a release liner 58b which extends from the recessed area 68.

FIG. 5a is a sectional view of one of the flaps 24 of the sanitary napkin 20 of FIG. 5 taken along section line 5a—5a. The flap adhesives 56 have been provided with a release liner 58b having a release portion 83 and a tab portion 84. The release portion 83 is removably secure to the flap adhesive 56 and the tab portion 84 extends from the mouth 76 of the recessed area 68 when the flap 24 is tucked into the recessed area 68 as shown in FIGS. 5 and 5a. Pulling upon the tab portion 84 of the release liner 58b, causes the flap 24 to be drawn out of the recessed area 68. Pulling upon the tab portion 84 of the release liner 58b, preferably also causes the flap adhesive 56 to separate from the release portion 83 of the release liner 58b. The tab portion 84 is generally compliant, soft-feeling and non-irritating to the user's skin. The tab portion 84 is preferably made from any of the materials conventionally used for sanitary napkins 20. Preferably the tab portion 84 will be comprised of the same material as the release liner 58b. In a preferred embodiment the tab portion 84 will simply be an extension of the release liner 58b.

Although release liners are generally not used with mechanical fastening materials, a mechanical fastening material may be provided with a release liner. If a flap securement member comprising a mechanical fastener (not shown) is tucked into the recessed area such that the distal edge of the flap is positioned in the recessed area and will not form a tab member, it is preferred that the mechanical fastening material of the securement member be provided with a release liner comprising a tab portion and a release portion. The release portion will be removably secured to the mechanical fastening material and at least a portion of the tab portion will extend outside of the recessed area to form a tab member. The release portion will preferably comprise a fibrous material such as the loop fastening materials which are well known in the art. The tab portion will comprise any material which is compliant, soft, non-irritating to the skin, and which is strong enough to pull the flap out of the recessed are without breaking, rupturing, etc. Preferably, the tab portion will be comprised of those materials commonly used for sanitary napkins.

Figure 6:
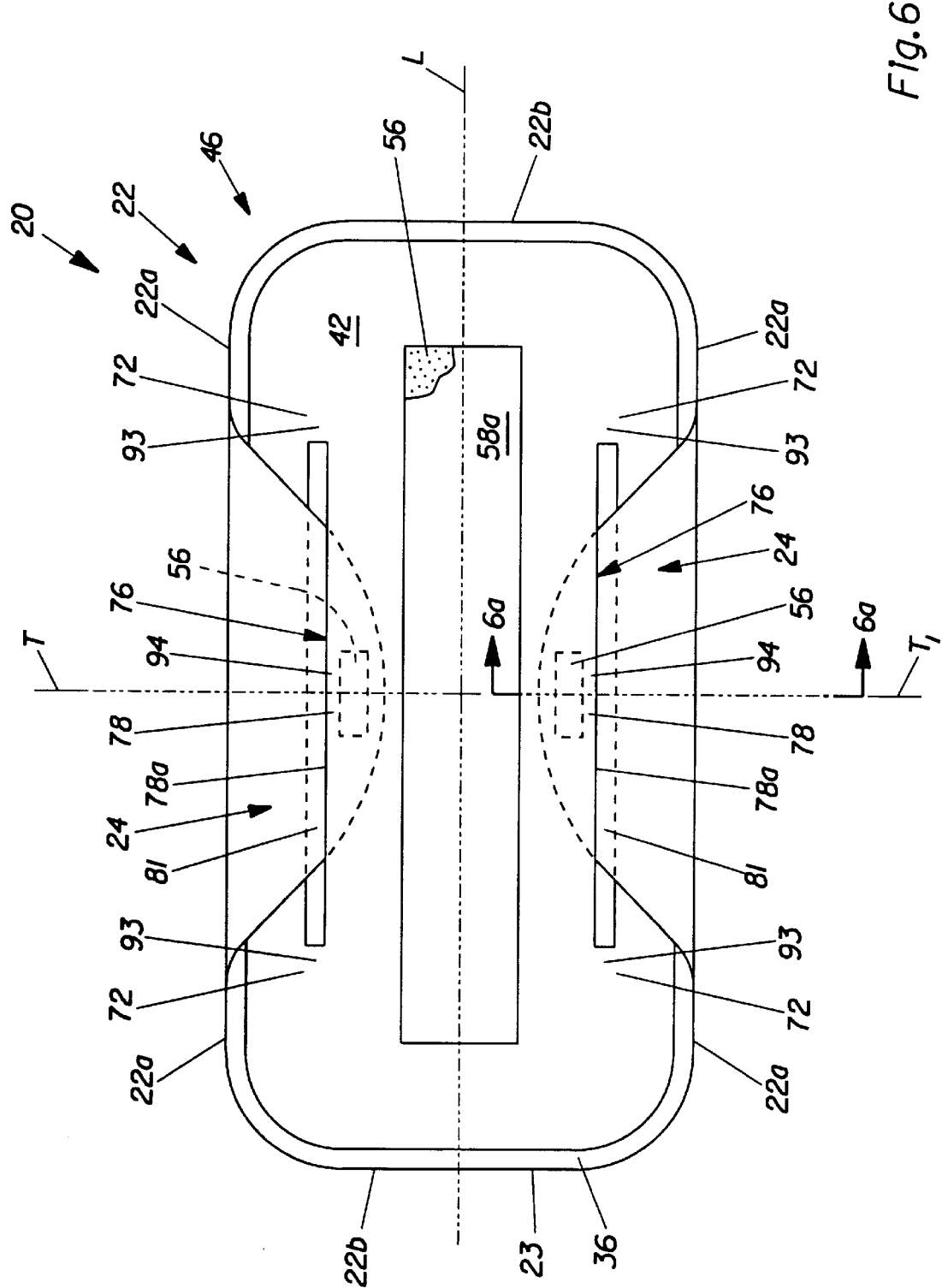
FIG. 6 is a plan view of another alternate sanitary napkin embodiment of the present invention with the garment side facing the viewer.

An alternative embodiment of the present invention is shown in FIGS. 6 and 6a. FIG. 6 is a plan view of a sanitary napkin 20 of the present invention with the garment side 20b facing the viewer and with the flap 24 tucked into the recessed area 68. The retaining member 78 is joined to the backsheet 42 of the absorbent assembly 46 at a portion of the seam 36 which corresponds with the longitudinal edge 46a of the absorbent assembly 46. The point of connection 72 is preferably made at the same time as the seam 36 which joins the backsheet 42 to the topsheet 40. A portion of the center region 94 of the retaining member 78 is detached or decoupled from the backsheet 42. The recessed area 68 is formed between the decoupled center region 94 of the retaining member 78 and the backsheet 42 of the absorbent assembly 46.

The retaining member 78 has two longitudinally extending slits, cuts, or openings 81. Each of the openings 81 forms the mouth 76 of the recessed area 68. Each opening 81 is located about midway between the longitudinal edge 22a of the main body portion 22 and the principal longitudinal centerline L. However, each of the openings 81 may be located laterally closer to the principal longitudinal centerline L or the longitudinal edge 22a of the main body portion 22.

D. Function of the Sanitary Napkin With Respect to an Undergarment

The function of the sanitary napkin of the present invention will now be described in greater detail with relation to the wearer's undergarments.

Figure 4:
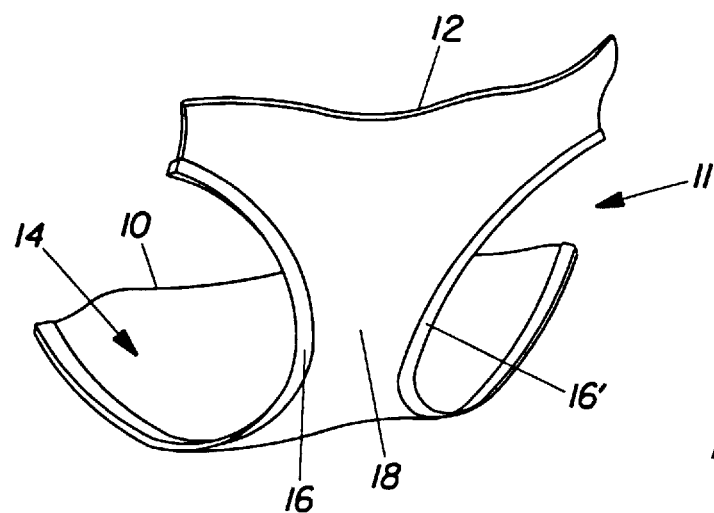
FIG. 4 is a perspective view of the crotch portion of a women's panties.

FIG. 4 is a depiction of the crotch portion 14 of an undergarment 11 of the type commonly worn by many women and well known as a panty. A panty 11 comprises a front section 10, a back section 12, and a crotch portion 14 which joins the front and back sections. The crotch portion 14 comprises two side edges 16 and center crotch portion 18.

Figure 4A:
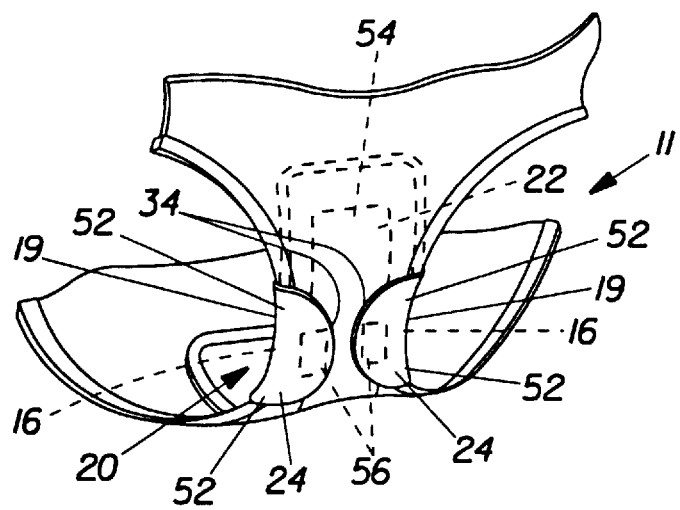
FIG. 4a is the same perspective view of the women's panties shown in FIG. 4 with the sanitary napkin embodiment of the present invention being placed therein for use, with the flaps extended and affixed to the underside of the panties.
Figure 4B:
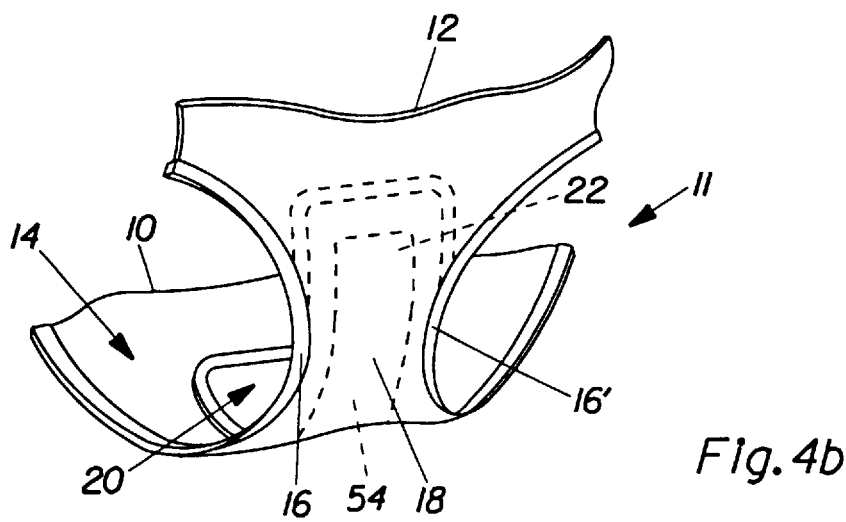
FIG. 4b is the same perspective view of the women's panties shown in FIG. 4 with the sanitary napkin embodiment of the present invention with the flaps tucked into the recessed areas, being placed therein for use.

The sanitary napkin 20 of the present invention may be utilized by removing the release liner 58a of the central pad adhesive 54 and placing the sanitary napkin 20 in a panty 11 as shown in FIG. 4b. The center of main body portion 22 is placed in crotch portion 14 of the panty with one end of main body portion 22 extending towards the front section 10 of the panty and the other end towards the back section 12. The backsheet 42 is placed in contact with the inner surface of center crotch portion 18 of the panty. Central pad adhesive 54 maintains main body portion 22 in position. The flaps 24 remain in the stored position. The panty is pulled up into position on the wearer's lower torso. Although, the flaps 24 have not been used and remain tucked into the recessed areas 68, the flaps 24 will not adversely effect the functionality of the sanitary napkin 20.

Alternatively, the sanitary napkin 20 of the present invention may be utilized by removing the release liner 58a from the central pad adhesive and placing the sanitary napkin 20 in a panty 11 as shown in FIG. 4a. The center of main body portion 22 is placed in crotch portion 14 of the panty with one end of main body portion 22 extending towards the front section 10 of the panty and the other end towards the back section 12. The backsheet 42 is placed in contact with the inner surface of center crotch portion 18 of the panty. Central pad adhesive 54 maintains main body portion 22 in position. The flaps 24 are removed from the recessed area 68. The release liners 58b are removed from the flap adhesives 56. The distal portions of flaps 24 are folded around the side edges 16 of the panty, and the flap adhesives 56 are secured to the underside of the panty.

In an alternative embodiment, the sanitary napkin 20 could be provided with an elastomer, such as an elastomeric strand, elastomeric ribbon, elastomeric film or the like. In such an embodiment the main body portion 22 would preferably comprise such an elastomer joined to at least a portion of each longitudinal edge 22a. A sanitary napkin comprising an elastomer is disclosed in U.S. patent application 07/811,348, "Elasticized Sanitary Napkin", filed Dec. 20, 1991, in the name of Diane Sneller, June Brennock, and Carl Bergman, which patent application is incorporated herein by reference.

E. Zones of Differential Extensibility

In the most preferred case, the sanitary napkin will have at least one zone of differential extensibility (or "zone of extensibility", or simply "zone") 50. Preferably, as shown in FIG. 3, the sanitary napkin 20 has four zones of differential extensibility 50, one in each quarter of the sanitary napkin 20. The zones of differential extensibility 50 are preferably located along a portion of the fold line where the flaps 24 are folded around the wearer's panty crotch. The fold line will typically be located along or adjacent the longitudinal juncture 30 of each flap 24. Since the terms "portions", "zones", and "regions", as used herein, refer to general areas, the zones of differential extensibility 50 and the corner regions 52 are, thus, not limited to points which lie precisely on the lines of juncture 30. Typically, they will include both those points which lie on the lines of juncture 30 as well as the surrounding areas of the sanitary napkin 20 (which include the aforementioned fold lines). The longitudinal junctures, thus, typically serve as good approximations for the location of the zones of differential extensibility 50.

The corner regions 52 are designated as such because they typically include the "corners" formed along the periphery 23 of the sanitary napkin 20. The "corners" occur where the edges 35 of the flaps 24 intersect with the longitudinal side edges 22a of the main body portion 22 when the sanitary napkin 20 is shown in a plan view. It is not necessary for there to be a sharp angle formed at the intersection of these edges, or for lines of demarcation to designate the same, however. (Another way to describe the corner regions 52 is with reference to U.S. Pat. No. 4,917,697 issued to Osborn, III, et al. The corner regions 52 described herein are typically comprised at least of those areas shown as having slits or notches in the Osborn, et al. patent. (For simplicity, these areas may be referred to herein as "notch regions"). However, the corner regions 52 in the present invention preferably encompass a larger area than the slits or notches shown in the Osborn patent.)

The portions of the flaps 24 in the corner regions 52 of the sanitary napkin 20 may be referred to as the "corner regions of the flaps" or "flap corner regions". These may be separately designated 52' although they are still considered to comprise the corner regions 52, per se.

FIGS. 3, 3a, and 3b show an embodiment of the present invention which has one preferred type of zones of differential extensibility 50. In the embodiment shown in FIGS. 3, 3a, and 3b, the zones of differential extensibility 50 comprise portions of the sanitary napkin 20 that have slack provided therein. These portions of the sanitary napkin 20 comprise at least the flap corner regions 52'.

The slack is provided to the sanitary napkin 20 in the embodiment shown in FIGS. 3, 3a, and 3b by pleating and then restraining portions of the flaps. The flaps 24 are pleated or folded with generally longitudinally-oriented fold lines 62. The fold lines 62 can run along and/or outboard (or even inboard) of the juncture 30 of the flaps and the main body portion 22. The pleats preferably run the length of the juncture 30. The pleated sections of the flaps (the "pleats") 64 are preferably folded on top of each other (that is, stacked perpendicular to the plane of the sanitary napkin). In alternative embodiments, they may be folded and arranged side-by-side. The pleated sections are gathered in or restrained from opening by a flap pleat restraint 66 located along the flap transverse centerline $T_1$. This provides the sanitary napkin, and particularly the flaps 24, with corner regions 52 which are extensible in the transverse direction and with center portions 27 (along the flap transverse centerline $T_1$) which are not.

The zones of differential extensibility 50 are most preferably located at those points where the edges 35 of the flaps 24 intersect the edges 16 of the panty when the sanitary napkin 20 is worn. The points of intersection can generally be determined by having a person wear a particularly designed napkin having flaps and a fairly commonly designed panty. Commonly, panties have a crotch width of about 5.0 to about 9.0 centimeters. Marks can then be made on the bottom surface of the sanitary napkin 20 where the sanitary napkin 20 intersects the panty. The points of intersection between the flap 24 and the edge 16 of the panty generally coincide with the ends of the fold. Assuming the napkin has two flaps, the four marks will mark the general locations for the zones of differential extensibility 50. The zones of differential extensibility 50 may be located along the lines of juncture 30, outboard of the lines of juncture in the flaps 24, or inboard of the lines of juncture. Commonly, the zones of differential extensibility 50 will begin at a point located between the area of the flap transverse centerline $T_1$ and about 1.5 centimeters in the longitudinal direction from the flap transverse centerline $T_1$.

The zones of differential extensibility 50 may be of any shape. Typically, they will form a three-sided figure (roughly triangular, pie-shaped, or fan-shaped) in plan view when they are fully extended. Often, the figure defined by the zones of differential extensibility will have two sides that are of approximately equal length and a shorter side. The edge 35 of the flaps 24 usually forms the shorter side. It should be understood, however, that the precise shape of the zones of differential extensibility 50 is not always as critical as the location and extensibility properties of the same. Likewise, it is not critical for there to be precise lines of demarcation that mark the boundaries of the zones of differential extensibility 50 (or the boundaries of the complementary first portions of the quarters of the sanitary napkin). Thus, there can be a gradual transition between the zones of differential extensibility 50 and the first portions of the quarters of the sanitary napkin.

The zones of differential extensibility 50 may be bounded on one side by the line of juncture 30. Alternatively, the boundary may be adjacent the line of juncture 30. If the zones of differential extensibility 50 are provided in the main body portion 22 (for instance, if they are formed by a fold made through the main body portion 22 (as described below)), however, this boundary may be as far inboard as the principal longitudinal centerline L. The zones of differential extensibility 50 are typically bounded at the ends by at least a portion of the edge 35 of the flap 24. This is often a curved line. (The zones of differential extensibility 50 can also be bounded at the ends by a portion of the longitudinal edges 22a of the main body portion and/or transverse or end edges 22b of the main body portion 22.) The third side of the zones of differential extensibility is typically formed by a boundary which may be an imaginary line that runs from the point of the zone of differential extensibility 50 which is either located on the flap transverse centerline $T_1$ (or nearest to the same), to a point on the edge 35 of the flap 24.

The total area covered by the zones of differential extensibility 50 can vary widely. The area can cover a relatively large portion of the sanitary napkin, provided there remain some portions of the sanitary napkin adjacent at least portions of the principal longitudinal centerline and the flap transverse centerline that are less extensible. The zones of differential extensibility 50 can be provided along the entire juncture 30 of the flaps 24 with the main body portion 22. In alternative embodiments, the zones of differential extensibility 50 can be provided throughout the entire flap (for instance, if the entire flap is pleated with longitudinally-oriented pleats). Preferably, however, in the present invention, zones of differential extensibility 50 are not provided either along the entire juncture 30 or throughout the entire flap. There are several reasons for this.

First, due to the curvature of the panty crotch, all portions of the flaps are not stressed the same amount when the flaps are wrapped around a panty crotch. Typically, the portion of the flaps located adjacent the flap transverse centerline $T_1$ (the center portion 27 of the flap) will not be subjected to stresses that are as great as those exerted on the flap corner regions 52'. Thus, it is possible that the center portion 27 of the flaps (and possibly also the adjacent regions of the main body portion 22) could be constructed so that it is not provided with any extensibility properties. Alternatively, the center portion 27 (and adjacent regions) could merely be less extensible than the corner regions 52 of the sanitary napkin.

Second, it is preferable that the corner regions 52' of the flaps 24 stretch a greater distance in the transverse direction than the center portion 27 of the flaps for the best fit and for the flaps 24 to adapt properly to the curvature of the crotch of the wearer's undergarments. This allows the boundary defined by the zones of differential extensibility to correspond to the configuration of the edges of the crotch of the wearer's panties.

Third, depending on the process used to create the zones of differential extensibility 50, it may be less expensive to provide differential extensibility in only certain portions of the sanitary napkins.

The amount of differential extensibility needed can vary depending on a number of factors. These include, but are not limited to the size and configuration of the wearer's panties, the size and configuration of the flaps, etc. Any amount of differential extensibility in the corner regions 52 will provide some benefit versus a sanitary napkin that is not provided with zones of differential extensibility. The amount of differential extensibility should not be so great, however, that the excess material that comprises the zones of differential extensibility 50 causes the sanitary napkin to fit sloppily adjacent the wearer's panties and her body.

Preferably, the amount of differential extensibility is sufficient to substantially reduce the stresses on the flaps when the sanitary napkin is worn. Typically, a conservatively configured zone of differential extensibility 50 is one which when fully extended, defines a linear boundary (i.e., one which forms a straight line) that runs from the intersection of the flap transverse centerline $T_1$ and the line of juncture 30 to the point on the edge 35 of the flap 24 where the flap 24 intersects the edge 16 of the panty crotch. A zone of differential extensibility 50 with a linear configuration is said to be conservatively configured because it will ordinarily provide a sufficient amount of extensibility in most cases to relieve the stresses in the flaps 24. In an ideal case, the boundary will correspond to the configuration of the edges 16 of the crotch of the wearer's panties.

Again referring to FIGS. 3, 3a, and 3b, the flaps 24 are pleated or folded with generally longitudinally-oriented fold lines 62. The pleated sections are gathered in or restrained from opening by a flap pleat restraint 66 located along the flap transverse centerline $T_1$. This provides the sanitary napkin, and particularly the flaps 24, with corner regions which are extensible in the transverse direction and with center portions 27 (along the flap transverse centerline $T_1$) which are not.

In such a pleated embodiment, the flaps 24 can be provided with any number of fold lines. For instance, in the most basic form of the pleated embodiment, the flaps can simply be folded inward toward the principal longitudinal centerline L along a single line along the juncture 30 and tacked to the main body portion 22 or the flap 24 itself, at a point inboard of the juncture 30 (which is preferably in the area of the flap transverse centerline $T_1$). Typically, however, as shown in FIG. 3, the flaps will have at least two pleat fold lines 62.

The flap pleat restraint 66 can be any suitable type of element capable of keeping a portion of the pleated material from unfolding. The flap pleat restraint 66 can be located along the flap transverse centerline $T_1$, or it can be spaced some distance away from the flap transverse centerline $T_1$. The flap pleat restraint 66 is, however, preferably located at some place along the flap transverse centerline $T_1$. This creates flaps with pleats which are able to open up an equal amount in both the front and back halves 26 and 28 for a preferred fit around the panty crotch. The flap pleat restraint 66 is also preferably located more toward the mouth 65 of each fold as opposed to the crease 67 of the fold as shown in FIG. 3a. The amount of differential extensibility of the flap 24 will increase as the flap pleat restraint 66 is positioned closer to the mouth 65 of the fold. The flaps 24 can have separate flap pleat restraints 66 located along (or spaced some distance away from) the flap transverse centerline $T_1$ for each flap, or they can have a single flap pleat restraint that spans from one flap to the other.

The flap pleat restraint 66 shown in FIG. 3 is an "interior" restraint, i.e., it is located in between two pleated or folded sections 64 of the flaps 24. In alternative embodiments, the flap pleat restraint 66 can be of a type which secures the pleated sections 64 of the flaps 24 from outside (or exterior) of the pleated sections.

The flap pleat restraint 66 may be of any size provided it is no larger than the length of the juncture 30. This allows the pleated sections 64 of the flaps 24 to open properly. This is the case since the pleated sections 64 of the flaps 24 will typically open from the ends of the lines of juncture to the flap pleat restraint 66. It may, therefore, be preferable for the flap pleat restraint 66 to be as small as possible to minimize interference with the opening of the pleated sections 64. The flap pleat restraint 66 should also be located at a point on the pleated section 64 that is relatively close to the principal longitudinal centerline L. This will ensure that the pleat will not unfold and lose its effectiveness.

The flap pleat restraint 66 can be of any suitable construction. Suitable flap pleat restraints 66 include, but are not limited to adhesives, ultrasonic bonds, heat and/or pressure bonds, tapes, etc. These different types of flap pleat restraints can be in an unlimited number of configurations. Such configurations can include spots, lines, patches, etc.

FIG. 3 shows an embodiment of the present invention having two recessed areas 68, one on each side of the principal longitudinal centerline L, and having four zones of differential extensibility, one in each quarter of the sanitary napkin 20. The zones of differential extensibility 50 are formed by folding the flaps 24 to form a pleat and securing each fold of the pleat along the principal transverse centerline T, using a flap pleat restraint 66.

Each of the flaps 24 of the sanitary napkin 20 of FIG. 3 is joined to the retaining member 78 along a line of juncture 30. The retaining member 78 is joined to the sanitary napkin 20 along lines of connection 72 to form the recessed areas 68. The line of juncture 30 of the flap 24 is represented by a line of demarcation between the flaps 24 and the retaining member 78. Although there is not a precise line of demarcation between the retaining member 78 and the flap 24, the line of juncture 30 for each flap 24 is located generally between the line of connection 72 of the retaining member 78 and that portion of the flap 24 which generally corresponds with the longitudinal edge 22a of the main body portion 22 when the flap 24 is extended out in an unfolded, unpleated configuration.

It is not necessary for the flaps 24 to be joined to the retaining member 78, and it should be understood that the flaps 24 may be joined to the topsheet 40, backsheet 42, or both, or may be joined to any other element of the sanitary napkin 20. However, in the preferred embodiments of the present invention, the flaps 24 will be joined to the retaining member 78. In the most preferred embodiment the flaps 24 will be integral with and extensions of the retaining member 78.

Referring to FIGS. 3, 3a, and 3b, each flap 24 of this embodiment has a first portion 95 and a second portion 96. The first portion 95 comprises a pleat 64 which is secured by flap pleat restraints 66. The second portion 96 comprises the flap adhesive 56 and may comprise an integral release material (though FIGS. 3a and 3b show a separate flap release liner 58b).

The first portion 95 of each flap 24 has two fold lines 62 that form the pleat 64. The first fold that forms the pleat 64 is made inward toward the garment side 20b of the sanitary napkin 20. The second fold that forms the pleat 64 is also made inward towards the garment side 20b of the sanitary napkin 20. The fold line 62 that is closest to the proximal edge 32 of the flap 24 when the first portion 95 is unfolded, comprises a first pleat-forming fold line 62'. The fold line 62 that is located farther away from the proximal edge 32 of the flap 24 when the first portion 95 is unfolded, comprises a second pleat-forming fold line 62".

The pleat 64 of the first portion 95 of the flap 24, is positioned inboard of the longitudinal edge 22a of the main body portion 22 when the sanitary napkin 20 is looked at from a top plan view such as in FIG. 3. This results in the pleat 64 of the first portion 95 being positioned in the recessed area 68 between the retaining member 78 and the backsheet 42 of the main body portion 22 when the flap 24 is extended as shown in FIG. 3a or when the flap is tucked as shown in FIG. 3b.

Again referring to FIGS. 3, 3a, and 3b, the second portion 96 of each flap 24 comprises a flap adhesive 56 and may comprise an integral release member. The flap adhesive 56 is positioned adjacent to the distal edge 34 of the flap 24 and the integral release member should be positioned adjacent to the first portion 95 of the flap 24, such that when the second portion 96 is folded along a longitudinally extending fold line 62, the flap adhesive 56 will superpose the integral release member and be removably secured thereto.

When the flap 24 is tucked into the recessed area 68 as shown in FIG. 3b, the second portion 96 will comprise two longitudinally extending fold lines 62. The fold line 62 located closest to the first portion 95 when the second portion is unfolded, comprises a first tuck-forming fold line 63. The fold line located farther away from the first portion of the flap 24 when the second portion is unfolded, comprises a second tuck-forming fold line 63'. The first tuck-forming fold line 63 is formed by folding the flap material of the second portion 96 towards the garment side 42b of the backsheet 42. The second tuck-forming fold line 63' is formed by folding the flap material of the second portion 96 toward the garment side 42b of the backsheet 42 and brings the flap adhesive 56 in face to face relation with the integral release member such that the flap adhesive is removably secured thereto. This results in the second portion 96 of the flap 24 being configured in an S-fold and being positioned in the recessed area 68 between the first portion 95 of the flap 24 and the backsheet 42 of the main body portion 22 with the distal edge 34 of the flap 24 being positioned at or near the mouth 76 of the recessed area 68. Preferably, when the flap is tucked into the recessed area 68 as shown in FIG. 3b, the distal edge 34 of the flap 24 will form a graspable tab member 90 which can be used to pull the second portion 96 of the flap 24 from the recessed area 68 and simultaneously peel the flap adhesive 56 from the integral release member.

Figure 7:
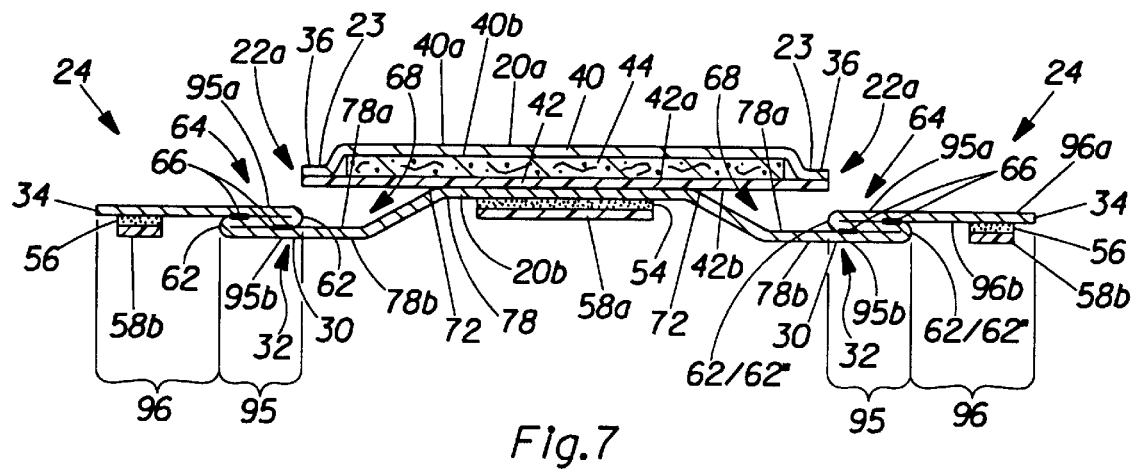
Figure 7A:
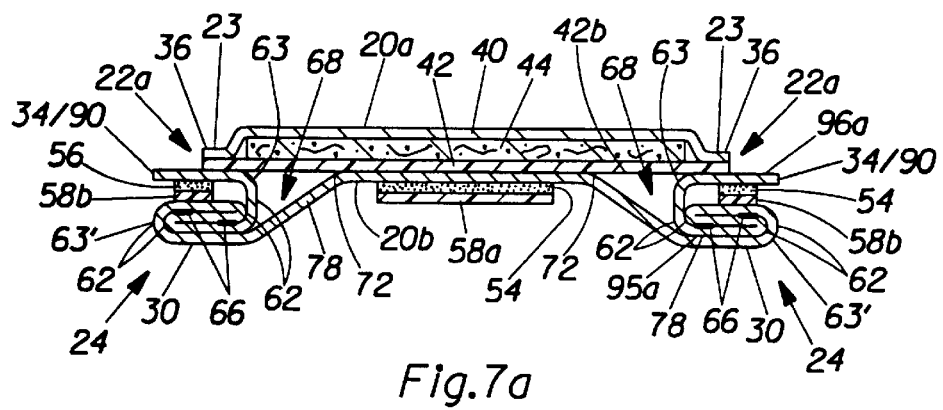
FIG. 7a is a cross-sectional view of the sanitary napkin embodiment of FIG. 7 showing the flaps tucked into the recessed areas in a folded and rolled configuration.

A transverse, cross-sectional view of a particularly preferred sanitary napkin embodiment of the present invention, is shown in FIGS. 7 and 7a. The embodiment shown in FIGS. 7 and 7a is similar to the embodiment shown in FIGS. 3–3b, i.e., the flaps 24 are extensions of the retaining member 78 which is joined to the backsheet 42 of the main body portion 22 along the lines of connection 72. However, the flaps 24 are arranged in a different configuration when they are tucked, as shown in FIG. 7a, and when they are extended, as shown in FIG. 7.

Referring to FIG. 7, each flap 24 may again be thought of as having a first portion 95 and a second portion 96. The first portion 95 of the flap 24 comprises a pleat 64 which is secured by the flap pleat restraints 66, and may comprise an integral release member (though FIG. 7 shows a separate flap release liner 58b) joined to the body-facing side 95b of the first portion 95. The second portion 96 comprises a flap adhesive 56 joined to the garment-facing side 96b of the second portion 96.

The pleat 64 of the first portion 95 of the flap 24, has two longitudinally extending fold lines 62. The fold line that is closest to the proximal edge 32 of the flap 24 when the first portion 95 is unfolded, comprises a first pleat-forming fold line 62'. The fold line 62 that is located farther away from the proximal edge 32 of the flap 24 when the first portion 95 is unfolded, comprises a second pleat-forming fold line 62". The first pleat-forming fold line 62' is formed by folding the flap material toward the garment-facing side 42b of the backsheet 42. The second pleat-forming fold line 62" is also formed by folding the flap material towards the garment-facing side 42b of the backsheet 42. The pleat 64 of the first portion 95 is secured by flap pleat restraints 66 which are located substantially adjacent the mouth of each fold. The first portion 95 of the flap 24 also comprises an integral release member which is joined to the garment-facing side 95b of the first portion 95.

The first portion 95 of the flap 24 is positioned outboard of the longitudinal edge 22a of the main body portion 22 when the sanitary napkin 20 is looked at from a top plan view. This results in the first portion 95 being positioned outside of the recessed area 68 when the flap 24 is extended as shown in FIG. 7. The second portion 96 of each flap 24 comprises a flap adhesive 56. The flap adhesive 56 is positioned substantially adjacent to the distal edge 34 of the flap 24 and is positioned on the garment-facing side 96b of the second portion 96.

When the flap 24 is tucked into the recessed area 68 as shown in FIG. 7a, the second portion 96 will be folded along a first tuck-forming fold line 63 such that the flap adhesive 56 of the second portion 96 and may superpose any integral release member of the first portion 95. The first portion 95 and the second portion 96 are then folded toward the garment-facing side 42b of the backsheet 42 to form a second tuck-forming fold line 63'. As shown in FIG. 7a, this results in the body-facing side 95a of the first portion 95 being in substantially face to face relation with the body-facing side 78a of the retaining member 78, and the body-facing side 96a of the second portion 96 being in substantially face to face relation with the garment side 42b of the backsheet 42. Accordingly, this results in the first portion 95 and second portion 96 of the flap 24, being positioned in the recessed area 68 between the retaining member 78 and the backsheet 42 of the sanitary napkin 20. Preferably, as shown in FIG. 7a, when the flap 24 is tucked into the recessed area 68, the distal edge 34 of the flap 24 will form a graspable tap member 90.

Other methods of providing zones of differential extensibility, are discussed in greater detail in commonly-assigned, co-pending, U.S. patent application Ser. No. 07/769,891, "Absorbent Article Having Flaps and Zones of Differential Extensibility", filed Oct. 1, 1991, in the name of Bruce W. Lavash, et al., and in commonly-assigned, co-pending, U.S. patent application Ser. No. 07/832,246, "Absorbent Article Having Inwardly-Folded Pleated Flaps", filed Feb. 7, 1992, in the name of Kaoru Niihara and Thomas W. Osborn, III, which patent applications are incorporated herein by reference.

Thus, the present invention provides a sanitary napkin having a retaining member joined to an absorbent assembly to form a recessed area wherein the flaps may be tucked.

While particular embodiments of the present invention have been illustrated and described, it would be obvious to those skilled in the art that various other changes and modifications can be made without departing from the spirit and scope of the invention.

What is claimed is:

1. An absorbent article having a body-facing side, a garment side, two spaced apart longitudinal sides between said body-facing side and said garment side, a principal longitudinal centerline, and a principal transverse centerline, said absorbent article comprising:

a main body portion having two spaced apart longitudinal edges, two spaced apart transverse edges, a first end region, a second end region, and a central region disposed between said end regions, said main body portion comprising:

an absorbent assembly comprising a liquid pervious topsheet, a liquid impervious backsheet joined to said topsheet, and an absorbent core positioned between said topsheet and said backsheet; and a first retaining member and a second retaining member joined to said absorbent assembly, each of said first retaining member and said second retaining member comprising two end regions, a center region positioned between and joined to said end regions, and a longitudinal edge, at least a portion of each of said end regions being joined to said absorbent assembly at a point of connection, at least a portion of said center region being decoupled from said absorbent assembly to form a first recessed area between said center region of said first retaining member and said absorbent assembly and to form a second recessed area between said center region of said second retaining member and said absorbent assembly;

a first flap and a second flap, each of said first flap and said second flap being joined along a line of juncture to said main body portion and having a proximal edge adjacent the line of juncture, a distal edge disposed away from the line of juncture, and a flap transverse centerline that passes through said central region of said main body portion, a portion of said first flap being capable of being tucked into said first recessed area and a portion of said second flap being capable of being tucked into said second recessed area; and a zone of differential extensibility comprising a portion of at least one of said flaps that is capable of greater extensibility outward in a generally transverse direction than points on said flaps which are located along said flap transverse centerline adjacent said proximal edge of said flap.

2. The absorbent article of claim 1 where said zone of differential extensibility comprises material that has slack therein.

3. The absorbent article of claim 1 where said zone of differential extensibility comprises extensible material.

4. The absorbent article of claim 1 where said zone of differential extensibility comprises pre-strained portion of said absorbent article which has been permanently elongated.

5. The absorbent article of claim 1 where said zone of differential extensibility comprises pre-corrugated or ring-rolled portions of said absorbent article.

6. The absorbent article of claim 1 where said zone of differential extensibility is located entirely within one of said flaps.

7. The absorbent article of claim 1 where said zone of differential extensibility is located partially with one of said flaps and partially within said main body portion.

8. The absorbent article of claim 1 where said flap transverse centerline divides said flap into halves, and each half of said flaps comprises a zone of differential extensibility.

* * * * *